United States Patent
Genovese et al.

(10) Patent No.: US 11,701,228 B2
(45) Date of Patent: *Jul. 18, 2023

(54) FLEXIBLE CANOPY VALVE REPAIR SYSTEMS AND METHODS OF USE

(71) Applicant: MEDTRONIC VASCULAR, INC., Santa Rosa, CA (US)

(72) Inventors: Matthew Genovese, Windsor, CA (US); Jeffrey Sandstrom, Scandia, MN (US); Russell Pribanic, Roxbury, CT (US); Thomas McPeak, Caledonia, MN (US); Vania Lee, Circle Pines, MN (US); Dermot O'Brien, Galway (IE); James Calvin Allan, Boise, ID (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 210 days.

This patent is subject to a terminal disclaimer.

(21) Appl. No.: 17/339,353

(22) Filed: Jun. 4, 2021

(65) Prior Publication Data

US 2021/0290390 A1 Sep. 23, 2021

Related U.S. Application Data

(63) Continuation of application No. 16/352,963, filed on Mar. 14, 2019, now Pat. No. 11,026,791.

(Continued)

(51) Int. Cl.
*A61F 2/24* (2006.01)
*A61B 17/04* (2006.01)
*A61B 17/00* (2006.01)

(52) U.S. Cl.
CPC .......... *A61F 2/2454* (2013.01); *A61F 2/2457* (2013.01); *A61F 2/2463* (2013.01);

(Continued)

(58) Field of Classification Search
CPC .... A61F 2/2454; A61F 2/2457; A61F 2/2463; A61F 2/2412; A61B 17/0401; A61B 2017/00243

See application file for complete search history.

(56) References Cited

U.S. PATENT DOCUMENTS

| 6,165,183 A | 12/2000 | Kuehen et al. |
| 6,260,552 B1 | 7/2001 | Mortier et al. |

(Continued)

FOREIGN PATENT DOCUMENTS

| WO | 2012068541 A2 | 5/2012 |
| WO | 2017115123 A1 | 7/2017 |

OTHER PUBLICATIONS

The International Search Report and Written Opinion dated Aug. 9, 2019 in International Appln. No. PCT/US2019/022680.

*Primary Examiner* — Suba Ganesan
(74) *Attorney, Agent, or Firm* — Medler Ferrro Woodhouse & Mills PLLC

(57) ABSTRACT

A system for treating valvular regurgitation in a heart valve includes a flexible canopy and an elongated tether including an elastic portion and an inelastic portion. When the system is in a deployed configuration, a proximal end of the flexible canopy is coupled to an annulus of the heart valve and a distal end of the elongated tether is coupled to a ventricle. The flexible canopy is configured to overlay a first native leaflet of the heart valve, and tension on the elongated tether is applied and/or adjusted to prevent the first leaflet from prolapsing, to maximize coaptation of the flexible canopy with a second native leaflet of the heart valve, and to minimize regurgitation of the heart valve.

20 Claims, 17 Drawing Sheets

Related U.S. Application Data

(60) Provisional application No. 62/645,306, filed on Mar. 20, 2018.

(52) U.S. Cl.
CPC . *A61B 17/0401* (2013.01); *A61B 2017/00243* (2013.01); *A61F 2/2412* (2013.01); *A61F 2230/0095* (2013.01); *A61F 2250/0018* (2013.01)

(56) References Cited

U.S. PATENT DOCUMENTS

| | | |
|---|---|---|
| 6,269,819 B1 | 8/2001 | Oz et al. |
| 6,312,447 B1 | 11/2001 | Grimes |
| 6,332,893 B1 | 12/2001 | Mortier et al. |
| 6,355,030 B1 | 3/2002 | Aldrich et al. |
| 6,402,781 B1 | 6/2002 | Langberg et al. |
| 6,406,420 B1 | 6/2002 | McCarthy et al. |
| 6,419,696 B1 | 7/2002 | Ortiz et al. |
| 6,461,366 B1 | 10/2002 | Seguin |
| 6,537,314 B2 | 3/2003 | Langberg et al. |
| 6,575,971 B2 | 6/2003 | Hauck et al. |
| 6,602,288 B1 | 8/2003 | Cosgrove et al. |
| 6,619,291 B2 | 9/2003 | Hlavka et al. |
| 6,626,930 B1 | 9/2003 | Allen et al. |
| 6,629,534 B1 | 10/2003 | St. Goar et al. |
| 6,656,221 B2 | 12/2003 | Taylor et al. |
| 6,676,702 B2 | 1/2004 | Mathis |
| 6,689,164 B1 | 2/2004 | Seguin et al. |
| 6,695,866 B1 | 2/2004 | Kuehen et al. |
| 6,702,826 B2 | 3/2004 | Liddicoat et al. |
| 6,706,065 B2 | 3/2004 | Langberg et al. |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,743,239 B1 | 6/2004 | Keuhn et al. |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,770,083 B2 | 8/2004 | Seguin |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,797,002 B2 | 9/2004 | Spence et al. |
| 6,800,090 B2 | 10/2004 | Alferness et al. |
| 6,805,711 B2 | 10/2004 | Quijano et al. |
| 6,810,882 B2 | 11/2004 | Langberg et al. |
| 6,824,562 B2 | 11/2004 | Mathis et al. |
| 6,840,246 B2 | 1/2005 | Downing |
| 6,875,224 B2 | 4/2005 | Grimes |
| 6,890,353 B2 | 5/2005 | Cohn et al. |
| 6,908,478 B2 | 6/2005 | Alferness et al. |
| 6,913,608 B2 | 7/2005 | Liddicoat et al. |
| 6,926,715 B1 | 8/2005 | Hauck et al. |
| 6,926,730 B1 | 8/2005 | Nguyen et al. |
| 6,949,122 B2 | 9/2005 | Adams et al. |
| 6,960,229 B2 | 11/2005 | Mathis et al. |
| 6,962,605 B2 | 11/2005 | Cosgrove et al. |
| 6,964,683 B2 | 11/2005 | Kowalsky et al. |
| 6,964,684 B2 | 11/2005 | Ortiz et al. |
| 6,966,926 B2 | 11/2005 | Mathis |
| 6,976,995 B2 | 12/2005 | Mathis et al. |
| 6,978,176 B2 | 12/2005 | Lattouf |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,004,958 B2 | 2/2006 | Adams et al. |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,044,967 B1 | 5/2006 | Solem et al. |
| 7,052,487 B2 | 5/2006 | Cohn et al. |
| 7,070,618 B2 | 7/2006 | Streeter |
| 7,077,861 B2 | 7/2006 | Spence |
| 7,077,862 B2 | 7/2006 | Vidlund et al. |
| 7,083,628 B2 | 8/2006 | Bachman |
| 7,090,695 B2 | 8/2006 | Solem et al. |
| 7,094,244 B2 | 8/2006 | Schreck |
| 7,112,207 B2 | 9/2006 | Allen et al. |
| 7,112,219 B2 | 9/2006 | Vidlund et al. |
| 7,122,043 B2 | 10/2006 | Greenhalgh et al. |
| 7,125,420 B2 | 10/2006 | Rourke et al. |
| 7,166,126 B2 | 1/2007 | Spence et al. |
| 7,166,127 B2 | 1/2007 | Spence et al. |
| 7,179,282 B2 | 2/2007 | Alferness et al. |
| 7,179,291 B2 | 2/2007 | Rourke et al. |
| 7,186,264 B2 | 3/2007 | Liddicoat et al. |
| 7,189,199 B2 | 3/2007 | McCarthy et al. |
| 7,192,442 B2 | 3/2007 | Solem et al. |
| 7,192,443 B2 | 3/2007 | Solem et al. |
| 7,211,110 B2 | 5/2007 | Rowe et al. |
| 7,226,467 B2 | 6/2007 | Lucatero et al. |
| 7,229,469 B1 | 6/2007 | Witzel et al. |
| 7,247,134 B2 | 7/2007 | Vidlund et al. |
| 7,270,676 B2 | 9/2007 | Alferness et al. |
| 7,288,097 B2 | 10/2007 | Seguin |
| 7,291,168 B2 | 11/2007 | Macoviak et al. |
| 7,296,577 B2 | 11/2007 | Lashinski et al. |
| 7,300,462 B2 | 11/2007 | Swinford et al. |
| 7,309,354 B2 | 12/2007 | Mathis et al. |
| 7,311,728 B2 | 12/2007 | Solem et al. |
| 7,311,729 B2 | 12/2007 | Mathis et al. |
| 7,311,731 B2 | 12/2007 | Lesniak et al. |
| 7,314,485 B2 | 1/2008 | Mathis |
| 7,316,706 B2 | 1/2008 | Bloom et al. |
| 7,351,259 B2 | 4/2008 | Swinford et al. |
| 7,351,260 B2 | 4/2008 | Nieminen et al. |
| 7,357,815 B2 | 4/2008 | Shaoulian et al. |
| 7,361,190 B2 | 4/2008 | Shaoulian et al. |
| 7,364,588 B2 | 4/2008 | Mathis et al. |
| 7,373,207 B2 | 5/2008 | Lattouf |
| 7,377,941 B2 | 5/2008 | Rhee et al. |
| 7,381,210 B2 | 6/2008 | Zarbatany et al. |
| 7,381,220 B2 | 6/2008 | Macoviak et al. |
| 7,396,364 B2 | 7/2008 | Moaddeb et al. |
| 7,404,824 B1 | 7/2008 | Webler et al. |
| 7,431,692 B2 | 10/2008 | Zollinger et al. |
| 7,431,726 B2 | 10/2008 | Spence et al. |
| 7,442,207 B2 | 10/2008 | Rafiee |
| 7,452,375 B2 | 11/2008 | Mathis et al. |
| 7,464,712 B2 | 12/2008 | Oz et al. |
| 7,473,274 B2 | 1/2009 | Sater |
| 7,485,143 B2 | 2/2009 | Webler et al. |
| 7,500,989 B2 | 3/2009 | Solem et al. |
| 7,503,931 B2 | 3/2009 | Kowalsky et al. |
| 7,503,932 B2 | 3/2009 | Mathis et al. |
| 7,507,252 B2 | 3/2009 | Lashinski et al. |
| 7,509,959 B2 | 3/2009 | Oz et al. |
| 7,510,576 B2 | 3/2009 | Langberg et al. |
| 7,510,577 B2 | 3/2009 | Moaddeb et al. |
| 7,513,908 B2 | 4/2009 | Lattouf |
| 7,527,646 B2 | 5/2009 | Rahdert et al. |
| 7,527,647 B2 | 5/2009 | Spence |
| 7,534,204 B2 | 5/2009 | Starksen et al. |
| 7,534,260 B2 | 5/2009 | Lattouf |
| 7,536,228 B2 | 5/2009 | Shaolian et al. |
| 7,559,936 B2 | 7/2009 | Levine et al. |
| 7,563,267 B2 | 7/2009 | Goldfarb et al. |
| 7,563,273 B2 | 7/2009 | Goldfarb et al. |
| 7,569,062 B1 | 8/2009 | Kuehen et al. |
| 7,588,582 B2 | 9/2009 | Ancora |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,120 B2 | 10/2009 | Adams et al. |
| 7,628,797 B2 | 12/2009 | Tieu et al. |
| 7,635,329 B2 | 12/2009 | Goldfarb et al. |
| 7,635,386 B1 | 12/2009 | Gammie |
| 7,635,387 B2 | 12/2009 | Reuter et al. |
| 7,637,945 B2 | 12/2009 | Solem et al. |
| 7,637,946 B2 | 12/2009 | Solem et al. |

(56) References Cited

U.S. PATENT DOCUMENTS

| | | |
|---|---|---|
| 7,655,015 B2 | 2/2010 | Goldfarb et al. |
| 7,655,040 B2 | 2/2010 | Douk et al. |
| 7,666,193 B2 | 2/2010 | Starksen et al. |
| 7,666,204 B2 | 2/2010 | Thornton et al. |
| 7,666,224 B2 | 2/2010 | Vidlund et al. |
| 7,674,287 B2 | 3/2010 | Alferness et al. |
| 7,682,319 B2 | 3/2010 | Martin et al. |
| 7,682,369 B2 | 3/2010 | Seguin |
| 7,695,510 B2 | 4/2010 | Bloom et al. |
| 7,695,512 B2 | 4/2010 | Lashinski et al. |
| 7,699,892 B2 | 4/2010 | Rafiee et al. |
| 7,704,277 B2 | 4/2010 | Zakay et al. |
| 7,713,298 B2 | 5/2010 | Shaoulian et al. |
| 7,717,954 B2 | 5/2010 | Solem et al. |
| 7,722,523 B2 | 5/2010 | Mortier et al. |
| 7,722,668 B2 | 5/2010 | Moaddeb et al. |
| 7,736,388 B2 | 6/2010 | Goldfarb et al. |
| 7,744,609 B2 | 6/2010 | Allen et al. |
| 7,744,611 B2 | 6/2010 | Nguyen et al. |
| 7,753,858 B2 | 7/2010 | Starksen et al. |
| 7,753,922 B2 | 7/2010 | Starksen |
| 7,753,923 B2 | 7/2010 | St. Goar et al. |
| 7,753,924 B2 | 7/2010 | Starksen et al. |
| 7,758,595 B2 | 7/2010 | Allen et al. |
| 7,758,596 B2 | 7/2010 | Oz et al. |
| 7,758,637 B2 | 7/2010 | Starksen et al. |
| 7,758,639 B2 | 7/2010 | Mathis |
| 7,766,812 B2 | 8/2010 | Schroeder et al. |
| 7,785,366 B2 | 8/2010 | Maurer et al. |
| 7,794,496 B2 | 9/2010 | Gordon et al. |
| 7,803,187 B2 | 9/2010 | Hauser |
| 7,806,928 B2 | 10/2010 | Rowe et al. |
| 7,811,296 B2 | 10/2010 | Goldfarb et al. |
| 7,814,635 B2 | 10/2010 | Gordon et al. |
| 7,828,841 B2 | 11/2010 | Mathis et al. |
| 7,828,842 B2 | 11/2010 | Nieminen et al. |
| 7,828,843 B2 | 11/2010 | Alferness et al. |
| 7,837,728 B2 | 11/2010 | Nieminen et al. |
| 7,837,729 B2 | 11/2010 | Gordon et al. |
| 7,857,846 B2 | 12/2010 | Alferness et al. |
| 7,871,368 B2 | 1/2011 | Zollinger et al. |
| 7,871,433 B2 | 1/2011 | Lattouf |
| 7,883,538 B2 | 2/2011 | To et al. |
| 7,887,552 B2 | 2/2011 | Bachman |
| 7,887,582 B2 | 2/2011 | Mathis et al. |
| 7,914,544 B2 | 3/2011 | Nguyen et al. |
| 7,922,762 B2 | 4/2011 | Starksen |
| 7,927,370 B2 | 4/2011 | Webler et al. |
| 7,931,684 B2 | 4/2011 | Cosgrove et al. |
| 7,935,146 B2 | 5/2011 | Langberg et al. |
| 7,938,827 B2 | 5/2011 | Hauck et al. |
| 7,942,927 B2 | 5/2011 | Kaye et al. |
| 7,942,928 B2 | 5/2011 | Webler et al. |
| 7,955,384 B2 | 6/2011 | Rafiee et al. |
| 7,981,020 B2 | 7/2011 | Mortier et al. |
| 7,981,123 B2 | 7/2011 | Seguin |
| 7,988,725 B2 | 8/2011 | Gross et al. |
| 7,988,726 B2 | 8/2011 | Langberg et al. |
| 7,993,397 B2 | 8/2011 | Lashinski et al. |
| 7,998,151 B2 | 8/2011 | St. Goar et al. |
| 8,016,882 B2 | 9/2011 | Macoviak et al. |
| 8,029,565 B2 | 10/2011 | Lattouf |
| 8,043,368 B2 | 10/2011 | Crabtree |
| 8,052,592 B2 | 11/2011 | Goldfarb et al. |
| 8,057,493 B2 | 11/2011 | Goldfarb et al. |
| 8,062,313 B2 | 11/2011 | Kimblad |
| 8,062,358 B2 | 11/2011 | Mathis et al. |
| 8,066,766 B2 | 11/2011 | To et al. |
| 8,070,746 B2 | 12/2011 | Orton et al. |
| 8,070,805 B2 | 12/2011 | Vidlund et al. |
| 8,075,616 B2 | 12/2011 | Solem et al. |
| 8,092,363 B2 | 1/2012 | Leinsing et al. |
| 8,092,525 B2 | 1/2012 | Eliasen et al. |
| 8,096,985 B2 | 1/2012 | Legaspi et al. |
| 8,100,964 B2 | 1/2012 | Spence |
| 8,109,984 B2 | 2/2012 | Solem et al. |
| 8,123,703 B2 | 2/2012 | Martin et al. |
| 8,128,691 B2 | 3/2012 | Keränen |
| 8,133,239 B2 | 3/2012 | Oz et al. |
| 8,133,272 B2 | 3/2012 | Hyde |
| 8,142,493 B2 | 3/2012 | Spence et al. |
| 8,142,494 B2 | 3/2012 | Rahdert et al. |
| 8,147,542 B2 | 4/2012 | Maisano et al. |
| 8,163,013 B2 | 4/2012 | Machold et al. |
| 8,172,856 B2 | 5/2012 | Eigler et al. |
| 8,172,898 B2 | 5/2012 | Alferness et al. |
| 8,182,529 B2 | 5/2012 | Gordon et al. |
| 8,187,207 B2 | 5/2012 | Machold et al. |
| 8,187,266 B2 | 5/2012 | Dickens et al. |
| 8,187,299 B2 | 5/2012 | Goldfarb et al. |
| 8,187,323 B2 | 5/2012 | Mortier et al. |
| 8,202,315 B2 | 6/2012 | Hlavka et al. |
| 8,211,171 B2 | 7/2012 | Kim et al. |
| 8,216,230 B2 | 7/2012 | Hauck et al. |
| 8,216,256 B2 | 7/2012 | Raschdorf et al. |
| 8,216,302 B2 | 7/2012 | Wilson et al. |
| 8,216,303 B2 | 7/2012 | Navia |
| 8,226,709 B2 | 7/2012 | Groothuis et al. |
| 8,226,711 B2 | 7/2012 | Mortier et al. |
| 8,241,304 B2 | 8/2012 | Bachman |
| 8,241,351 B2 | 8/2012 | Cabiri |
| 8,252,050 B2 | 8/2012 | Maisano et al. |
| 8,262,724 B2 | 9/2012 | Seguin et al. |
| 8,277,502 B2 | 10/2012 | Miller et al. |
| 8,287,555 B2 | 10/2012 | Starksen et al. |
| 8,287,557 B2 | 10/2012 | To et al. |
| 8,303,608 B2 | 11/2012 | Goldfarb et al. |
| 8,303,622 B2 | 11/2012 | Alkhatib |
| 8,323,334 B2 | 12/2012 | Deem et al. |
| 8,328,798 B2 | 12/2012 | Witzel et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,353,956 B2 | 1/2013 | Miller et al. |
| 8,357,195 B2 | 1/2013 | Kuehn |
| 8,361,086 B2 | 1/2013 | Allen et al. |
| 8,382,829 B1 | 2/2013 | Call et al. |
| 8,388,680 B2 | 3/2013 | Starksen et al. |
| 8,409,273 B2 | 4/2013 | Thornton et al. |
| 8,425,504 B2 | 4/2013 | Orton et al. |
| 8,439,971 B2 | 5/2013 | Reuter et al. |
| 8,449,606 B2 | 5/2013 | Eliasen et al. |
| 8,454,656 B2 | 6/2013 | Tuval |
| 8,454,683 B2 | 6/2013 | Rafiee et al. |
| 8,460,370 B2 | 6/2013 | Zakay et al. |
| 8,460,371 B2 | 6/2013 | Hlavka et al. |
| 8,470,028 B2 | 6/2013 | Thornton et al. |
| 8,475,472 B2 | 7/2013 | Bachman |
| 8,486,136 B2 | 7/2013 | Maurer et al. |
| 8,500,761 B2 | 8/2013 | Goldfarb et al. |
| 8,500,800 B2 | 8/2013 | Maisano et al. |
| 8,506,623 B2 | 8/2013 | Wilson et al. |
| 8,506,624 B2 | 8/2013 | Vidlund et al. |
| 8,518,107 B2 | 8/2013 | Tsukashima et al. |
| 8,523,881 B2 | 9/2013 | Cabiri et al. |
| 8,540,620 B2 | 9/2013 | Mortier et al. |
| 8,545,414 B2 | 10/2013 | Fitzgerald et al. |
| 8,545,553 B2 | 10/2013 | Zipory et al. |
| 8,551,161 B2 | 10/2013 | Dolan |
| 8,579,967 B2 | 11/2013 | Webler et al. |
| 8,579,968 B1 | 11/2013 | Shannon et al. |
| 8,591,460 B2 | 11/2013 | Wilson et al. |
| 8,608,797 B2 | 12/2013 | Gross et al. |
| 8,632,585 B2 | 1/2014 | Seguin et al. |
| 8,641,727 B2 | 2/2014 | Ancora |
| 8,647,254 B2 | 2/2014 | Callas et al. |
| 8,663,322 B2 | 3/2014 | Keränen |
| 8,690,858 B2 | 4/2014 | Machold et al. |
| 8,690,939 B2 | 4/2014 | Miller et al. |
| 8,709,074 B2 | 4/2014 | Solem et al. |
| 8,715,342 B2 | 5/2014 | Zipory et al. |
| 8,721,665 B2 | 5/2014 | Oz et al. |
| 8,728,097 B1 | 5/2014 | Sugimoto et al. |
| 8,734,467 B2 | 5/2014 | Miller et al. |

(56) References Cited

U.S. PATENT DOCUMENTS

| | | |
|---|---|---|
| 8,734,505 B2 | 5/2014 | St. Goar et al. |
| 8,740,918 B2 | 6/2014 | Seguin |
| 8,740,920 B2 | 6/2014 | Goldfarb et al. |
| 8,753,373 B2 | 6/2014 | Chau et al. |
| 8,758,257 B2 | 6/2014 | Cecere et al. |
| 8,758,393 B2 | 6/2014 | Zentgraf |
| 8,758,432 B2 | 6/2014 | Solem et al. |
| 8,771,292 B2 | 7/2014 | Allen et al. |
| 8,777,966 B2 | 7/2014 | Dale et al. |
| 8,778,016 B2 | 7/2014 | Janovsky et al. |
| 8,778,017 B2 | 7/2014 | Eliasen et al. |
| 8,784,482 B2 | 7/2014 | Rahdert et al. |
| 8,784,483 B2 | 7/2014 | Navia |
| 8,790,394 B2 | 7/2014 | Miller et al. |
| 8,795,298 B2 | 8/2014 | Hernlund et al. |
| 8,795,352 B2 | 8/2014 | O'Beirne et al. |
| 8,808,368 B2 | 8/2014 | Maisano et al. |
| 8,821,570 B2 | 9/2014 | Dumontelle et al. |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,858,622 B2 | 10/2014 | Machold et al. |
| 8,858,623 B2 | 10/2014 | Miller et al. |
| 8,864,822 B2 | 10/2014 | Spence et al. |
| 8,888,843 B2 | 11/2014 | Khairkhanan et al. |
| 8,888,844 B2 | 11/2014 | Eliasen et al. |
| 8,894,705 B2 | 11/2014 | Eliasen et al. |
| 8,911,461 B2 | 12/2014 | Traynor et al. |
| 8,911,494 B2 | 12/2014 | Hammer et al. |
| 8,920,322 B2 | 12/2014 | Mansi et al. |
| 8,926,695 B2 | 1/2015 | Gross et al. |
| 8,926,696 B2 | 1/2015 | Cabiri et al. |
| 8,926,697 B2 | 1/2015 | Gross et al. |
| 8,932,348 B2 | 1/2015 | Solem et al. |
| 8,938,283 B2 | 1/2015 | Zentgraf et al. |
| 8,940,042 B2 | 1/2015 | Miller et al. |
| 8,940,044 B2 | 1/2015 | Hammer et al. |
| 8,945,177 B2 | 2/2015 | Dell et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,956,406 B2 | 2/2015 | Subramanian et al. |
| 8,956,407 B2 | 2/2015 | Macoviak et al. |
| 8,961,597 B2 | 2/2015 | Subramanian et al. |
| 8,968,335 B2 | 3/2015 | Robinson et al. |
| 8,968,393 B2 | 3/2015 | Rothstein |
| 8,974,445 B2 | 3/2015 | Warnking et al. |
| 8,974,525 B2 | 3/2015 | Nieminen et al. |
| 8,979,923 B2 | 3/2015 | Spence et al. |
| 8,979,925 B2 | 3/2015 | Chang et al. |
| 8,992,605 B2 | 3/2015 | Zakai et al. |
| 8,998,794 B2 | 4/2015 | Mortier et al. |
| 8,998,933 B2 | 4/2015 | Rothstein et al. |
| 9,011,463 B2 | 4/2015 | Adams et al. |
| 9,011,468 B2 | 4/2015 | Ketai et al. |
| 9,011,520 B2 | 4/2015 | Miller et al. |
| 9,011,530 B2 | 4/2015 | Reich et al. |
| 9,011,531 B2 | 4/2015 | Rourke et al. |
| 9,044,221 B2 | 6/2015 | Zentgraf et al. |
| 9,044,246 B2 | 6/2015 | Goldfarb et al. |
| 9,050,187 B2 | 6/2015 | Sugimoto et al. |
| 9,060,858 B2 | 6/2015 | Thornton et al. |
| 9,066,710 B2 | 6/2015 | Dale et al. |
| 9,107,658 B2 | 8/2015 | Schaller et al. |
| 9,107,750 B2 | 8/2015 | Cartledge et al. |
| 9,119,718 B2 | 9/2015 | Keränen |
| 9,119,719 B2 | 9/2015 | Zipory et al. |
| 9,125,632 B2 | 9/2015 | Loulmet et al. |
| 9,125,653 B2 | 9/2015 | Kovach |
| 9,131,928 B2 | 9/2015 | Zlotnick et al. |
| 9,131,939 B1 | 9/2015 | Call et al. |
| 9,168,137 B2 | 10/2015 | Subramanian et al. |
| 9,173,646 B2 | 11/2015 | Fabro |
| 9,179,896 B2 | 11/2015 | Machold et al. |
| 9,180,005 B1 | 11/2015 | Lashinski et al. |
| 9,180,006 B2 | 11/2015 | Keranen |
| 9,180,007 B2 | 11/2015 | Reich et al. |
| 9,180,008 B2 | 11/2015 | Yellin et al. |
| 9,192,374 B2 | 11/2015 | Zentgraf |
| 9,192,471 B2 | 11/2015 | Bolling |
| 9,192,472 B2 | 11/2015 | Gross et al. |
| 9,198,757 B2 | 12/2015 | Schroeder et al. |
| 9,216,018 B2 | 12/2015 | Sutherland et al. |
| 9,226,787 B2 | 1/2016 | Merryman et al. |
| 9,226,825 B2 | 1/2016 | Starksen et al. |
| 9,232,942 B2 | 1/2016 | Seguin et al. |
| 9,232,998 B2 | 1/2016 | Wilson et al. |
| 9,237,886 B2 | 1/2016 | Seguin et al. |
| 9,254,141 B2 | 2/2016 | Morris et al. |
| 9,259,218 B2 | 2/2016 | Robinson |
| 9,259,261 B2 | 2/2016 | Boronyak et al. |
| 9,259,317 B2 | 2/2016 | Wilson et al. |
| 9,265,608 B2 | 2/2016 | Miller et al. |
| 9,271,833 B2 | 3/2016 | Kim et al. |
| 9,277,994 B2 | 3/2016 | Miller et al. |
| 9,282,964 B1 | 3/2016 | Cohen et al. |
| 9,301,842 B2 | 4/2016 | Bielefeld |
| 9,314,242 B2 | 4/2016 | Bachman |
| 9,320,600 B2 | 4/2016 | Nieminen et al. |
| 9,326,857 B2 | 5/2016 | Cartledge et al. |
| 9,345,470 B2 | 5/2016 | Tuval |
| 9,351,830 B2 | 5/2016 | Gross et al. |
| 9,358,111 B2 | 6/2016 | Spence et al. |
| 9,358,112 B2 | 6/2016 | Hlavka et al. |
| 9,370,424 B2 | 6/2016 | Call et al. |
| 9,393,080 B2 | 7/2016 | Zentgraf et al. |
| 9,402,721 B2 | 8/2016 | Buchbinder et al. |
| 9,408,695 B2 | 8/2016 | Mathis et al. |
| 9,414,852 B2 | 8/2016 | Gifford et al. |
| 9,414,918 B2 | 8/2016 | Chau et al. |
| 9,414,921 B2 | 8/2016 | Miller et al. |
| 9,421,098 B2 | 8/2016 | Gifford et al. |
| 9,421,099 B2 | 8/2016 | Dolan |
| 9,427,237 B2 | 8/2016 | Oz et al. |
| 9,433,503 B2 | 9/2016 | Tsukashima et al. |
| 9,445,898 B2 | 9/2016 | Tuval et al. |
| 9,452,048 B2 | 9/2016 | O'Beirne et al. |
| 9,474,605 B2 | 10/2016 | Rowe et al. |
| 9,474,606 B2 | 10/2016 | Zipory et al. |
| 9,474,608 B2 | 10/2016 | Mathis et al. |
| 9,492,276 B2 | 11/2016 | Lee et al. |
| 9,498,228 B2 | 11/2016 | Dale et al. |
| 9,498,330 B2 | 11/2016 | Solem |
| 9,498,331 B2 | 11/2016 | Chang et al. |
| 9,504,570 B2 | 11/2016 | Hauser et al. |
| 9,510,829 B2 | 12/2016 | Goldfarb et al. |
| 9,510,837 B2 | 12/2016 | Seguin |
| 9,510,946 B2 | 12/2016 | Chau et al. |
| 9,510,948 B2 | 12/2016 | Padala et al. |
| 9,526,613 B2 | 12/2016 | Gross et al. |
| 9,526,614 B2 | 12/2016 | Keränen |
| 9,526,616 B2 | 12/2016 | Nieminen et al. |
| 9,532,874 B2 | 1/2017 | Griffin et al. |
| 9,545,305 B2 | 1/2017 | Wilson et al. |
| 9,561,104 B2 | 2/2017 | Miller et al. |
| 9,561,105 B2 | 2/2017 | Rowe |
| 9,572,666 B2 | 2/2017 | Basude et al. |
| 9,572,667 B2 | 2/2017 | Solem |
| 9,579,200 B2 | 2/2017 | Lederman et al. |
| 9,592,118 B2 | 3/2017 | Khairkhahan et al. |
| 9,592,122 B2 | 3/2017 | Zipory et al. |
| 9,597,184 B2 | 3/2017 | Machold et al. |
| 9,610,082 B2 | 4/2017 | Morris et al. |
| 9,610,161 B2 | 4/2017 | Macoviak et al. |
| 9,610,162 B2 | 4/2017 | Zipory et al. |
| 9,610,163 B2 | 4/2017 | Khairkhahan et al. |
| 9,615,926 B2 | 4/2017 | Lashinski et al. |
| 9,616,197 B2 | 4/2017 | Serina et al. |
| 9,622,862 B2 | 4/2017 | Lashinski et al. |
| 9,636,106 B2 | 5/2017 | Meier et al. |
| 9,636,107 B2 | 5/2017 | Morales et al. |
| 9,636,223 B2 | 5/2017 | Khalil et al. |
| 9,636,224 B2 | 5/2017 | Zipory et al. |
| 9,642,706 B2 | 5/2017 | Eidenschink |

(56) References Cited

U.S. PATENT DOCUMENTS

| | | |
|---|---|---|
| 9,649,106 B2 | 5/2017 | Nobles et al. |
| 9,662,205 B2 | 5/2017 | Eidenschink |
| 9,662,208 B2 | 5/2017 | Padala et al. |
| 9,662,209 B2 | 5/2017 | Gross et al. |
| 9,706,996 B2 | 7/2017 | Nguyen et al. |
| 2001/0005787 A1 | 6/2001 | Oz et al. |
| 2002/0183837 A1 | 12/2002 | Streeter et al. |
| 2003/0105519 A1 | 6/2003 | Fasol et al. |
| 2003/0120340 A1 | 6/2003 | Liska et al. |
| 2003/0120341 A1 | 6/2003 | Shennib et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0044350 A1 | 3/2004 | Martin et al. |
| 2004/0102839 A1 | 5/2004 | Cohn et al. |
| 2004/0127982 A1 | 7/2004 | Machold et al. |
| 2004/0127983 A1 | 7/2004 | Mortier et al. |
| 2004/0133063 A1 | 7/2004 | McCarthy et al. |
| 2004/0133240 A1 | 7/2004 | Adams et al. |
| 2004/0152947 A1 | 8/2004 | Schroeder et al. |
| 2004/0153144 A1 | 8/2004 | Seguin et al. |
| 2004/0158321 A1 | 8/2004 | Reuter et al. |
| 2004/0162610 A1 | 8/2004 | Liska et al. |
| 2004/0167539 A1 | 8/2004 | Kuehen et al. |
| 2004/0210240 A1 | 10/2004 | Saint |
| 2004/0220654 A1 | 11/2004 | Mathis et al. |
| 2004/0220657 A1 | 11/2004 | Nieminen et al. |
| 2004/0243227 A1 | 12/2004 | Starksen et al. |
| 2004/0254600 A1 | 12/2004 | Zarbatany et al. |
| 2004/0260394 A1 | 12/2004 | Douk et al. |
| 2004/0267083 A1 | 12/2004 | McCarthy et al. |
| 2005/0027351 A1 | 2/2005 | Rueter et al. |
| 2005/0033446 A1 | 2/2005 | Deem et al. |
| 2005/0049679 A1 | 3/2005 | Taylor et al. |
| 2005/0070999 A1 | 3/2005 | Spence |
| 2005/0071000 A1 | 3/2005 | Liddicoat et al. |
| 2005/0075723 A1 | 4/2005 | Schroeder et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0137449 A1 | 6/2005 | Nieminen et al. |
| 2005/0137450 A1 | 6/2005 | Aronson et al. |
| 2005/0143811 A1 | 6/2005 | Realyvasquez |
| 2005/0148815 A1 | 7/2005 | Mortier et al. |
| 2005/0149014 A1 | 7/2005 | Hauck et al. |
| 2005/0159810 A1 | 7/2005 | Filsoufi |
| 2005/0177228 A1 | 8/2005 | Solem et al. |
| 2005/0184122 A1 | 8/2005 | Hlavka et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0209690 A1 | 9/2005 | Mathis et al. |
| 2005/0216039 A1 | 9/2005 | Lederman |
| 2005/0216078 A1 | 9/2005 | Starksen et al. |
| 2005/0222488 A1 | 10/2005 | Chang et al. |
| 2005/0222489 A1 | 10/2005 | Rahdert et al. |
| 2005/0228422 A1 | 10/2005 | Machold et al. |
| 2005/0240202 A1 | 10/2005 | Shennib et al. |
| 2005/0267529 A1 | 12/2005 | Crockett et al. |
| 2005/0267574 A1 | 12/2005 | Cohn et al. |
| 2005/0273138 A1 | 12/2005 | To et al. |
| 2005/0288777 A1 | 12/2005 | Rhee et al. |
| 2005/0288778 A1 | 12/2005 | Shaoulian et al. |
| 2006/0015178 A1 | 1/2006 | Moaddeb et al. |
| 2006/0025787 A1 | 2/2006 | Morales et al. |
| 2006/0069429 A1 | 3/2006 | Spence et al. |
| 2006/0100699 A1 | 5/2006 | Vidlund et al. |
| 2006/0106278 A1 | 5/2006 | Machold et al. |
| 2006/0106279 A1 | 5/2006 | Machold et al. |
| 2006/0122633 A1 | 6/2006 | To et al. |
| 2006/0136053 A1 | 6/2006 | Rourke et al. |
| 2006/0149368 A1 | 7/2006 | Spence |
| 2006/0161040 A1 | 7/2006 | McCarthy et al. |
| 2006/0161169 A1 | 7/2006 | Nieminen et al. |
| 2006/0167474 A1 | 7/2006 | Bloom et al. |
| 2006/0178700 A1 | 8/2006 | Quinn |
| 2006/0184230 A1 | 8/2006 | Solem et al. |
| 2006/0184242 A1 | 8/2006 | Lichtenstein |
| 2006/0195012 A1 | 8/2006 | Mortier et al. |
| 2006/0206203 A1 | 9/2006 | Yang et al. |
| 2006/0229708 A1 | 10/2006 | Powell et al. |
| 2006/0241745 A1 | 10/2006 | Solem |
| 2006/0241746 A1 | 10/2006 | Shaoulian et al. |
| 2006/0252984 A1 | 11/2006 | Rahdert et al. |
| 2006/0271174 A1 | 11/2006 | Nieminen et al. |
| 2006/0281968 A1 | 12/2006 | Duran et al. |
| 2006/0282161 A1 | 12/2006 | Huynh et al. |
| 2006/0293698 A1 | 12/2006 | Douk |
| 2007/0027533 A1 | 2/2007 | Douk |
| 2007/0038293 A1 | 2/2007 | St. Goar et al. |
| 2007/0038297 A1 | 2/2007 | Bobo et al. |
| 2007/0050022 A1 | 3/2007 | Vidlund et al. |
| 2007/0055206 A1 | 3/2007 | To et al. |
| 2007/0055368 A1 | 3/2007 | Rhee et al. |
| 2007/0061010 A1 | 3/2007 | Hauser et al. |
| 2007/0066863 A1 | 3/2007 | Rafiee et al. |
| 2007/0067027 A1 | 3/2007 | Moaddeb et al. |
| 2007/0073391 A1 | 3/2007 | Bourang et al. |
| 2007/0078297 A1 | 4/2007 | Rafiee et al. |
| 2007/0080188 A1 | 4/2007 | Spence et al. |
| 2007/0100356 A1 | 5/2007 | Lucatero et al. |
| 2007/0100439 A1 | 5/2007 | Cangialosi et al. |
| 2007/0112244 A1 | 5/2007 | McCarthy et al. |
| 2007/0112424 A1 | 5/2007 | Spence et al. |
| 2007/0118151 A1 | 5/2007 | Davidson |
| 2007/0118215 A1 | 5/2007 | Moaddeb |
| 2007/0129737 A1 | 6/2007 | Goldfarb et al. |
| 2007/0135913 A1 | 6/2007 | Moaddeb et al. |
| 2007/0156235 A1 | 7/2007 | Rourke et al. |
| 2007/0173926 A1 | 7/2007 | Bobo et al. |
| 2007/0185571 A1 | 8/2007 | Kapadia et al. |
| 2007/0198038 A1 | 8/2007 | Cohen et al. |
| 2007/0203391 A1 | 8/2007 | Bloom et al. |
| 2007/0213758 A1 | 9/2007 | Rourke et al. |
| 2007/0232941 A1 | 10/2007 | Rabinovich |
| 2007/0233238 A1 | 10/2007 | Huynh et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0255396 A1 | 11/2007 | Douk et al. |
| 2007/0265658 A1 | 11/2007 | Nelson et al. |
| 2007/0265702 A1 | 11/2007 | Lattouf |
| 2007/0270793 A1 | 11/2007 | Lattouf |
| 2007/0276437 A1 | 11/2007 | Call et al. |
| 2007/0276478 A1 | 11/2007 | Marmureanu et al. |
| 2007/0282429 A1 | 12/2007 | Hauser et al. |
| 2007/0293943 A1 | 12/2007 | Quinn |
| 2008/0004597 A1 | 1/2008 | Lattouf et al. |
| 2008/0015688 A1 | 1/2008 | Hill et al. |
| 2008/0039935 A1 | 2/2008 | Buch et al. |
| 2008/0050347 A1 | 2/2008 | Ichim |
| 2008/0065205 A1 | 3/2008 | Nguyen et al. |
| 2008/0091059 A1 | 4/2008 | Machold et al. |
| 2008/0091264 A1 | 4/2008 | Machold et al. |
| 2008/0140188 A1 | 6/2008 | Rahdert et al. |
| 2008/0140190 A1 | 6/2008 | Macoviak et al. |
| 2008/0167714 A1 | 7/2008 | St. Goar et al. |
| 2008/0177380 A1 | 7/2008 | Starksen et al. |
| 2008/0183283 A1 | 7/2008 | Downing |
| 2008/0183285 A1 | 7/2008 | Shaoulian et al. |
| 2008/0195126 A1 | 8/2008 | Solem |
| 2008/0195200 A1 | 8/2008 | Vidlund et al. |
| 2008/0200981 A1 | 8/2008 | Shaoulian et al. |
| 2008/0228032 A1 | 9/2008 | Starksen et al. |
| 2008/0228201 A1 | 9/2008 | Zarbatany et al. |
| 2008/0228265 A1 | 9/2008 | Spence et al. |
| 2008/0228266 A1 | 9/2008 | McNamara et al. |
| 2008/0228272 A1 | 9/2008 | Moaddeb et al. |
| 2008/0234701 A1 | 9/2008 | Morales et al. |
| 2008/0234702 A1 | 9/2008 | Morales et al. |
| 2008/0234813 A1 | 9/2008 | Heuser |
| 2008/0243150 A1 | 10/2008 | Starksen et al. |
| 2008/0249504 A1 | 10/2008 | Lattouf et al. |

(56) References Cited

U.S. PATENT DOCUMENTS

| | | |
|---|---|---|
| 2008/0249618 A1 | 10/2008 | Huynh et al. |
| 2008/0319541 A1 | 12/2008 | Filsoufi |
| 2009/0043381 A1 | 2/2009 | Macoviak et al. |
| 2009/0069885 A1 | 3/2009 | Rahdert et al. |
| 2009/0076600 A1 | 3/2009 | Quinn |
| 2009/0088838 A1 | 4/2009 | Shaolian et al. |
| 2009/0118744 A1 | 5/2009 | Wells et al. |
| 2009/0118825 A1 | 5/2009 | Rourke et al. |
| 2009/0149949 A1 | 6/2009 | Quinn |
| 2009/0177266 A1 | 7/2009 | Powell et al. |
| 2009/0182418 A1 | 7/2009 | Solem et al. |
| 2009/0182419 A1 | 7/2009 | Bolling |
| 2009/0209950 A1 | 8/2009 | Starksen |
| 2009/0216322 A1 | 8/2009 | Le et al. |
| 2009/0222081 A1 | 9/2009 | Linder et al. |
| 2009/0228100 A1 | 9/2009 | Solem et al. |
| 2009/0287179 A1 | 11/2009 | Machold et al. |
| 2009/0306622 A1 | 12/2009 | Machold et al. |
| 2009/0306685 A1 | 12/2009 | Fill |
| 2009/0326648 A1 | 12/2009 | Machold et al. |
| 2010/0023056 A1 | 1/2010 | Johansson et al. |
| 2010/0023118 A1 | 1/2010 | Medlock et al. |
| 2010/0030330 A1 | 2/2010 | Bobo et al. |
| 2010/0036483 A1 | 2/2010 | Rourke et al. |
| 2010/0049213 A1 | 2/2010 | Serina et al. |
| 2010/0094248 A1 | 4/2010 | Nguyen et al. |
| 2010/0121349 A1 | 5/2010 | Meier et al. |
| 2010/0121433 A1 | 5/2010 | Bolling et al. |
| 2010/0121435 A1 | 5/2010 | Subramanian et al. |
| 2010/0121437 A1 | 5/2010 | Subramanian et al. |
| 2010/0131057 A1 | 5/2010 | Subramanian et al. |
| 2010/0137887 A1 | 6/2010 | Crockett et al. |
| 2010/0152845 A1 | 6/2010 | Bloom et al. |
| 2010/0161044 A1 | 6/2010 | Chang et al. |
| 2010/0185172 A1 | 7/2010 | Fabro |
| 2010/0185273 A1 | 7/2010 | Solem et al. |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2010/0210899 A1 | 8/2010 | Schankereli |
| 2010/0217283 A1 | 8/2010 | St. Goar et al. |
| 2010/0249920 A1 | 9/2010 | Bolling et al. |
| 2010/0280602 A1 | 11/2010 | Mathis |
| 2010/0298929 A1 | 11/2010 | Thornton et al. |
| 2010/0298930 A1 | 11/2010 | Orlov |
| 2010/0318184 A1 | 12/2010 | Spence |
| 2010/0331971 A1 | 12/2010 | Keränen et al. |
| 2011/0009957 A1 | 1/2011 | Langberg et al. |
| 2011/0011917 A1 | 1/2011 | Loulmet |
| 2011/0015722 A1 | 1/2011 | Hauser et al. |
| 2011/0022164 A1 | 1/2011 | Quinn et al. |
| 2011/0022166 A1 | 1/2011 | Dahlgren et al. |
| 2011/0060407 A1 | 3/2011 | Ketai et al. |
| 2011/0066234 A1 | 3/2011 | Gordon et al. |
| 2011/0092988 A1 | 4/2011 | Cohen et al. |
| 2011/0093063 A1 | 4/2011 | Schreck |
| 2011/0106106 A1 | 5/2011 | Meier et al. |
| 2011/0106117 A1 | 5/2011 | Mathis et al. |
| 2011/0144743 A1 | 6/2011 | Lattouf |
| 2011/0172754 A1 | 7/2011 | Starksen et al. |
| 2011/0207996 A1 | 8/2011 | Starksen |
| 2011/0213387 A1 | 9/2011 | Nguyen et al. |
| 2011/0224784 A1 | 9/2011 | Quinn |
| 2011/0230961 A1 | 9/2011 | Langer et al. |
| 2011/0230962 A1 | 9/2011 | Moaddeb et al. |
| 2011/0251684 A1 | 10/2011 | Rahdert et al. |
| 2011/0257740 A1 | 10/2011 | Shaoulian et al. |
| 2011/0257741 A1 | 10/2011 | Moaddeb et al. |
| 2011/0264208 A1 | 10/2011 | Duffy et al. |
| 2012/0010461 A1 | 1/2012 | Goldfarb et al. |
| 2012/0041548 A1 | 2/2012 | Crabtree |
| 2012/0053680 A1 | 3/2012 | Bolling et al. |
| 2012/0065464 A1 | 3/2012 | Ellis et al. |
| 2012/0095552 A1 | 4/2012 | Spence et al. |
| 2012/0101442 A1 | 4/2012 | Legaspi et al. |
| 2012/0109288 A1 | 5/2012 | Bolling |
| 2012/0109289 A1 | 5/2012 | Bolling |
| 2012/0123532 A1 | 5/2012 | Mathis |
| 2012/0136433 A1 | 5/2012 | Marmureanu et al. |
| 2012/0158020 A1 | 6/2012 | Crockett et al. |
| 2012/0179184 A1 | 7/2012 | Orlov |
| 2012/0185040 A1 | 7/2012 | Rahdert et al. |
| 2012/0197388 A1* | 8/2012 | Khairkhahan ........ A61F 2/2466 623/2.11 |
| 2012/0203072 A1 | 8/2012 | Lattouf et al. |
| 2012/0209376 A1 | 8/2012 | Hauser et al. |
| 2012/0209379 A1 | 8/2012 | Shaolian et al. |
| 2012/0215305 A1 | 8/2012 | Le et al. |
| 2012/0221101 A1 | 8/2012 | Moaddeb et al. |
| 2012/0271331 A1 | 10/2012 | To et al. |
| 2012/0310331 A1 | 12/2012 | Eigler et al. |
| 2012/0323314 A1 | 12/2012 | Callas et al. |
| 2013/0023985 A1 | 1/2013 | Khairkhahan et al. |
| 2013/0035757 A1 | 2/2013 | Zentgraf et al. |
| 2013/0110230 A1 | 5/2013 | Solem |
| 2013/0116776 A1 | 5/2013 | Gross et al. |
| 2013/0123913 A1 | 5/2013 | Kuehn |
| 2013/0131791 A1 | 5/2013 | Hlavka et al. |
| 2013/0253639 A1 | 9/2013 | Alkhatib |
| 2013/0253641 A1 | 9/2013 | Lattouf |
| 2013/0282059 A1 | 10/2013 | Ketai et al. |
| 2013/0304093 A1 | 11/2013 | Serina et al. |
| 2013/0304197 A1 | 11/2013 | Buchbinder et al. |
| 2014/0039607 A1 | 2/2014 | Kovach |
| 2014/0066693 A1 | 3/2014 | Goldfarb et al. |
| 2014/0067048 A1 | 3/2014 | Chau et al. |
| 2014/0088693 A1 | 3/2014 | Seguin et al. |
| 2014/0135799 A1 | 5/2014 | Henderson |
| 2014/0148849 A1 | 5/2014 | Serina et al. |
| 2014/0155783 A1 | 6/2014 | Starksen et al. |
| 2014/0172084 A1 | 6/2014 | Callas et al. |
| 2014/0188108 A1 | 7/2014 | Goodine et al. |
| 2014/0207154 A1 | 7/2014 | Bielefeld et al. |
| 2014/0207161 A1 | 7/2014 | Dell et al. |
| 2014/0222138 A1 | 8/2014 | Machold et al. |
| 2014/0228871 A1 | 8/2014 | Cohen et al. |
| 2014/0243860 A1 | 8/2014 | Morris et al. |
| 2014/0243894 A1 | 8/2014 | Groothuis et al. |
| 2014/0243963 A1 | 8/2014 | Sheps et al. |
| 2014/0257341 A1 | 9/2014 | Eidenschink et al. |
| 2014/0275757 A1 | 9/2014 | Goodwin et al. |
| 2014/0276648 A1 | 9/2014 | Hammer et al. |
| 2014/0276971 A1 | 9/2014 | Kovach |
| 2014/0276979 A1 | 9/2014 | Sauer et al. |
| 2014/0309661 A1 | 10/2014 | Sheps et al. |
| 2014/0336756 A1 | 11/2014 | Lee et al. |
| 2014/0364875 A1 | 12/2014 | Zentgraf |
| 2014/0371843 A1 | 12/2014 | Wilson et al. |
| 2014/0379002 A1 | 12/2014 | Morris et al. |
| 2014/0379006 A1 | 12/2014 | Sutherland et al. |
| 2015/0018940 A1 | 1/2015 | Quill et al. |
| 2015/0018941 A1 | 1/2015 | Lee et al. |
| 2015/0032127 A1 | 1/2015 | Gammie et al. |
| 2015/0038988 A1 | 2/2015 | Tegels et al. |
| 2015/0045815 A1 | 2/2015 | Eidenschink |
| 2015/0051697 A1 | 2/2015 | Spence et al. |
| 2015/0057682 A1 | 2/2015 | Kovach |
| 2015/0066138 A1 | 3/2015 | Alexander et al. |
| 2015/0073547 A1 | 3/2015 | Eliasen et al. |
| 2015/0105804 A1 | 4/2015 | Dell et al. |
| 2015/0105855 A1 | 4/2015 | Cabiri et al. |
| 2015/0112432 A1 | 4/2015 | Reich et al. |
| 2015/0119981 A1 | 4/2015 | Khairkhahan et al. |
| 2015/0127091 A1 | 5/2015 | Cecere et al. |
| 2015/0133999 A1 | 5/2015 | Robinson et al. |
| 2015/0134050 A1 | 5/2015 | Solem et al. |
| 2015/0134053 A1 | 5/2015 | Morris et al. |
| 2015/0134055 A1 | 5/2015 | Spence et al. |
| 2015/0134057 A1 | 5/2015 | Rourke et al. |
| 2015/0142105 A1 | 5/2015 | Bolling et al. |
| 2015/0157459 A1 | 6/2015 | Macoviak et al. |
| 2015/0164639 A1 | 6/2015 | Starksen et al. |
| 2015/0173740 A1 | 6/2015 | Sugimoto et al. |
| 2015/0173900 A1 | 6/2015 | Hauser et al. |

(56) References Cited

U.S. PATENT DOCUMENTS

| | | |
|---|---|---|
| 2015/0182223 A1 | 7/2015 | Ketai et al. |
| 2015/0223793 A1 | 8/2015 | Goldfarb et al. |
| 2015/0272586 A1 | 10/2015 | Herman et al. |
| 2015/0272734 A1 | 10/2015 | Sheps et al. |
| 2015/0297212 A1 | 10/2015 | Reich et al. |
| 2015/0313713 A1 | 11/2015 | Zentgraf et al. |
| 2015/0335430 A1 | 11/2015 | Loulmet et al. |
| 2015/0366556 A1 | 12/2015 | Khairkhahan et al. |
| 2015/0366666 A1 | 12/2015 | Khairkhahan et al. |
| 2016/0008132 A1 | 1/2016 | Cabiri et al. |
| 2016/0015515 A1 | 1/2016 | Lashinski et al. |
| 2016/0015517 A1 | 1/2016 | Sutherland et al. |
| 2016/0022419 A1 | 1/2016 | Yellin et al. |
| 2016/0038285 A1 | 2/2016 | Glenn et al. |
| 2016/0038286 A1 | 2/2016 | Yellin et al. |
| 2016/0058557 A1 | 3/2016 | Reich et al. |
| 2016/0067043 A1 | 3/2016 | Machold et al. |
| 2016/0106420 A1 | 4/2016 | Foerster et al. |
| 2016/0113762 A1 | 4/2016 | Clague et al. |
| 2016/0113767 A1 | 4/2016 | Miller et al. |
| 2016/0120642 A1 | 5/2016 | Shaolian et al. |
| 2016/0143737 A1 | 5/2016 | Zentgraf et al. |
| 2016/0174979 A1 | 6/2016 | Wei |
| 2016/0192925 A1 | 7/2016 | Bachman |
| 2016/0242909 A1 | 8/2016 | Ketai et al. |
| 2016/0262887 A1 | 9/2016 | Chang et al. |
| 2016/0287387 A1 | 10/2016 | Wei |
| 2016/0354082 A1 | 12/2016 | Oz et al. |
| 2016/0374812 A1 | 12/2016 | Machold et al. |
| 2017/0007405 A1 | 1/2017 | Griffin et al. |
| 2017/0020521 A1 | 1/2017 | Krone et al. |
| 2017/0042546 A1 | 2/2017 | Goldfarb et al. |
| 2017/0049455 A1 | 2/2017 | Seguin |
| 2017/0055969 A1 | 3/2017 | Machold et al. |
| 2017/0143330 A1 | 5/2017 | Basude et al. |
| 2017/0189013 A1 | 7/2017 | Morris et al. |
| 2017/0202554 A1 | 7/2017 | Eidenschink |

\* cited by examiner

FLEXIBLE CANOPY VALVE REPAIR SYSTEMS AND METHODS OF USE

CROSS-REFERENCE TO RELATED APPLICATIONS

This application is a continuation of U.S. patent application Ser. No. 16/352,963, filed on Mar. 14, 2019, which claims the benefit of U.S. Provisional Patent Application Ser. No. 62/645,306, filed Mar. 20, 2018, which is hereby incorporated by reference in its entirety for all purposes.

FIELD OF THE INVENTION

The present technology relates generally to a system for repairing a valve suffering from regurgitation, and associated systems and methods.

BACKGROUND OF THE INVENTION

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs to the remaining body. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

The mitral valve, also known as the bicuspid or left atrioventricular valve, is a dual flap valve located between the left atrium and the left ventricle. The mitral valve serves to direct oxygenated blood from the lungs through the left side of the heart and into the aorta for distribution to the body. As with other valves of the heart, the mitral valve is a passive structure in that does not itself expend any energy and does not perform any active contractile function. The mitral valve includes two moveable leaflets, an anterior leaflet and a posterior leaflet, that each open and close in response to differential pressures on either side of the valve. Ideally, the leaflets move apart from each other when the valve is in an open configuration, and meet or "coapt" when the valve is in a closed configuration.

Diseases associated with heart valves, such as those caused by damage or a defect, can include stenosis and valvular insufficiency or regurgitation. These diseases can occur individually or concomitantly in the same valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

In particular, a large portion or percentage of degenerative regurgitation in a mitral valve is caused by a prolapsed posterior mitral leaflet. This can be caused by weakening or separation of the chordae attached to the posterior leaflet. In such cases, when the mitral valve is in the closed configuration, the posterior mitral leaflet billows or bulges like a sail or a parachute into the left atrium, causing the posterior leaflet to not fully coapt with the anterior mitral leaflet.

Currently, treatment options for the repair of a prolapsing leaflet includes re-sectioning of the prolapsed tissue, chordae repair, foldoplasty, annuloplasty, placement of a new valve, or attachment of a clip to couple a free end of the prolapsing leaflet to a free end of a non-prolapsing leaflet. However, these solutions have significant drawbacks in terms of efficacy, safety or likelihood of complications, invasiveness, reduction in the cross-sectional area for blood flow through the valve, and the availability of the valve for future treatments.

Accordingly, there is a need for systems that can repair a valve suffering from regurgitation due to a prolapsing leaflet more easily, with greater efficacy and fewer complications. Further, there is a need for systems that can repair a valve suffering from regurgitation due to a prolapsing leaflet while leaving the valve available for future treatments.

BRIEF SUMMARY OF THE INVENTION

Embodiments hereof are directed to a system for treating a valvular regurgitation in a heart valve. The system includes a flexible canopy and an elongated tether. A proximal end of the elongated tether is attached to a distal end of the flexible canopy. The flexible canopy includes a first surface and a second surface opposite the first surface. The elongated tether is configured to be placed under tension in situ and includes an inelastic portion and an elastic portion that is at least as long as the inelastic portion. When the system is in a deployed configuration, a proximal end of the flexible canopy is anchored to an annulus of a heart valve and a distal end of the elongated tether is anchored to tissue of a ventricle such that the first surface of the flexible canopy overlays an underlying first surface of a first leaflet of the heart valve. The elongated tether is placed under tension such that the system is configured to prevent the first leaflet of the heart valve from prolapsing, and to permit a portion of the second surface of the flexible canopy to coapt with at least an opposing mating portion of a second leaflet of the heart valve.

In another embodiment hereof, the system includes a flexible canopy and an elongated tether. A proximal end of the elongated tether is attached to a distal end of the flexible canopy. The flexible canopy includes a first surface and a second surface opposite the first surface. The flexible canopy is unsupported and does not include a frame attached thereto. The elongated tether is configured to be placed under tension in situ and includes an inelastic portion and an elastic portion. When the system is in a deployed configuration, a proximal end of the flexible canopy is anchored to an annulus of a heart valve and a distal end of the elongated tether is anchored to tissue of a ventricle such that the first surface of the flexible canopy overlays an underlying first surface of a first leaflet of the heart valve. The elongated tether is placed under tension such that the system is configured to prevent the first leaflet of the heart valve from prolapsing, and to permit a portion of the second surface of the flexible canopy to coapt with at least an opposing mating portion of a second leaflet of the heart valve.

Embodiments hereof are further directed to a method of treating a valvular regurgitation. The method includes percutaneously delivering a system in a delivery configuration to a heart valve. The system includes a flexible canopy and an elongated tether attached to a distal end of the flexible canopy. The flexible canopy is unsupported and does not include a frame coupled thereto and the elongated tether includes an inelastic portion and an elastic portion that is at least as long as the inelastic portion. At least one proximal anchor is embedded into an annulus of the heart valve. A proximal end of the flexible canopy is coupled to the at least one proximal anchor. A distal anchor is embedded into a ventricle adjacent to the heart valve. A distal end of the elongated tether is coupled to the distal anchor. A tension force is applied on the flexible canopy such that a first surface of the flexible canopy overlays an underlying first surface of a first leaflet of the heart valve. The heart valve is checked for regurgitation. The tension force on the flexible canopy is adjusted to minimize valvular regurgitation.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a delivery device, delivery system, or delivery catheter are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal", when used in the following description to refer to a system or a device to be implanted into a vessel, such as a system for treating heart valvular regurgitation, are used with reference to the direction of blood flow. Thus, "distal" and "distally" refer to positions in a downstream direction with respect to the direction of blood flow, and the terms "proximal" and "proximally" refer to positions in an upstream direction with respect to the direction of blood flow.

The following detailed description is merely exemplary in nature and is not intended to limit the present technology or the application and uses of the present technology. Although the description of embodiments hereof is in the context of treatment of heart valvular regurgitation and particularly in the context of treatment of regurgitation of the mitral valve, the present technology may also be used in any other body passageways where it is deemed useful. Furthermore, there is no intention to be bound by any expressed or implied theory presented in the preceding technical field, background, brief summary or the following detailed description.

Figure 1:
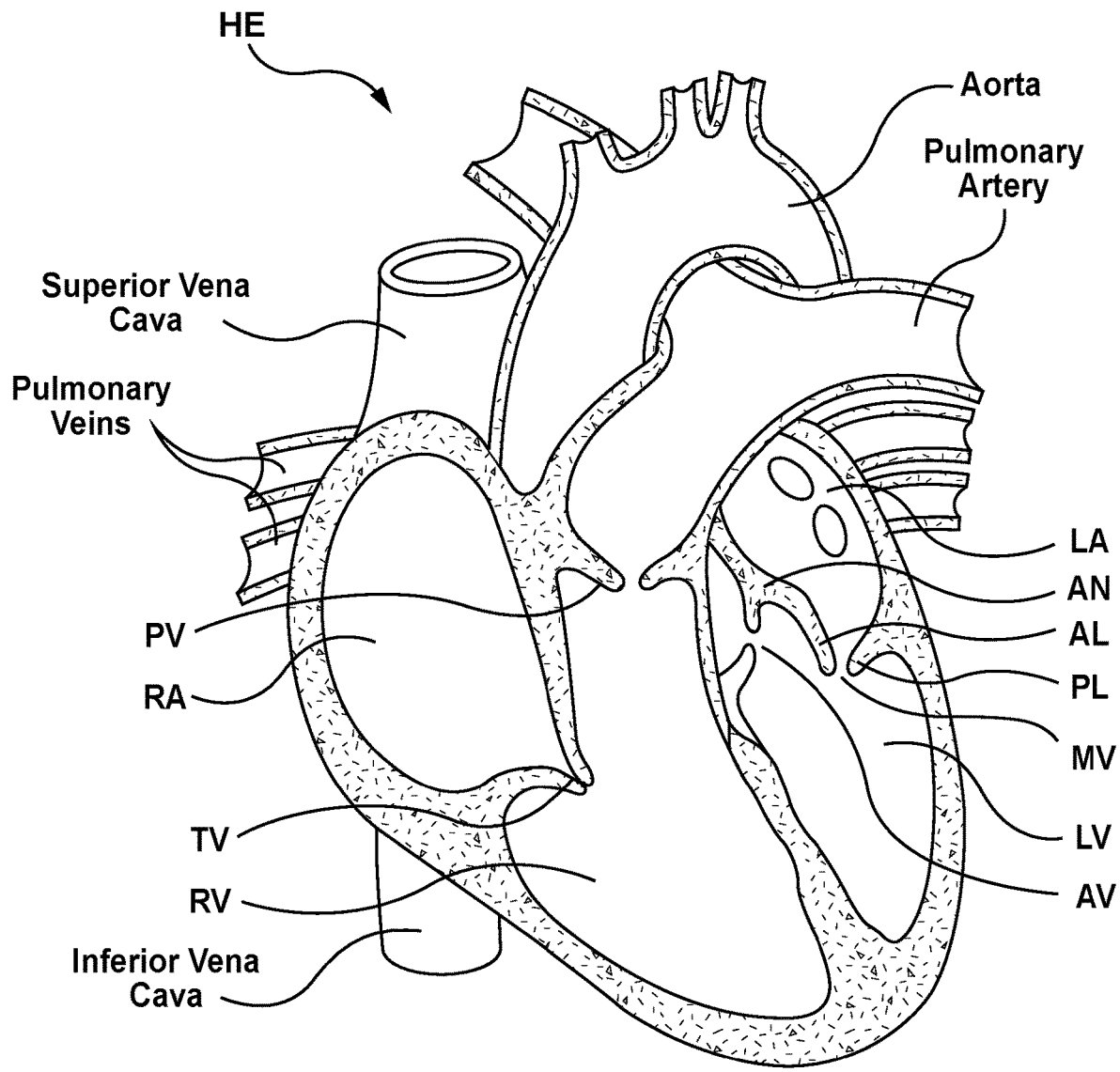
FIG. 1 is a schematic sectional illustration of a mammalian heart having native valve structures.
Figure 2B:
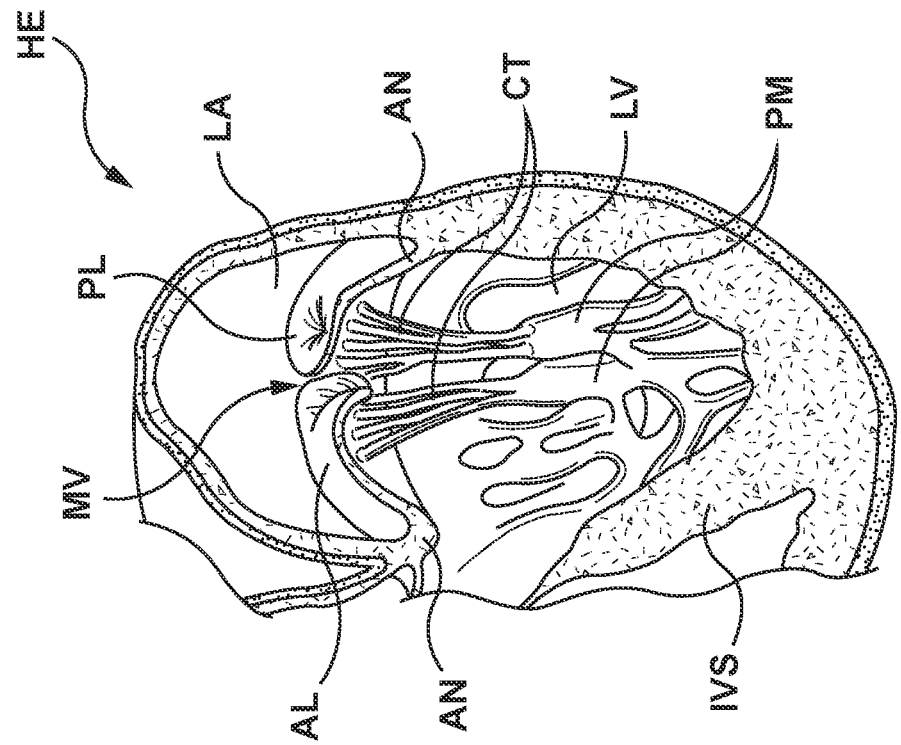
FIG. 2B is a schematic sectional illustration of the left ventricle of a heart having a prolapsed mitral valve in which the leaflets do not sufficiently coapt and which is suitable for repair with a system in accordance with embodiments hereof.
Figure 2A:
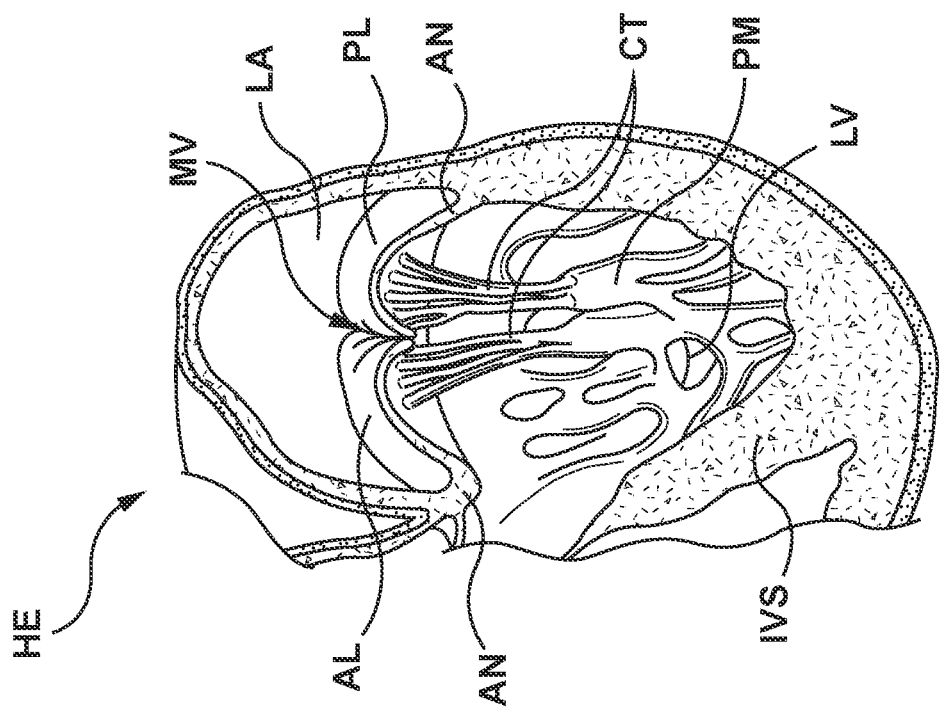
FIG. 2A is a schematic sectional illustration of a left ventricle of a mammalian heart showing anatomical structures and a native mitral valve.
Figure 2C:
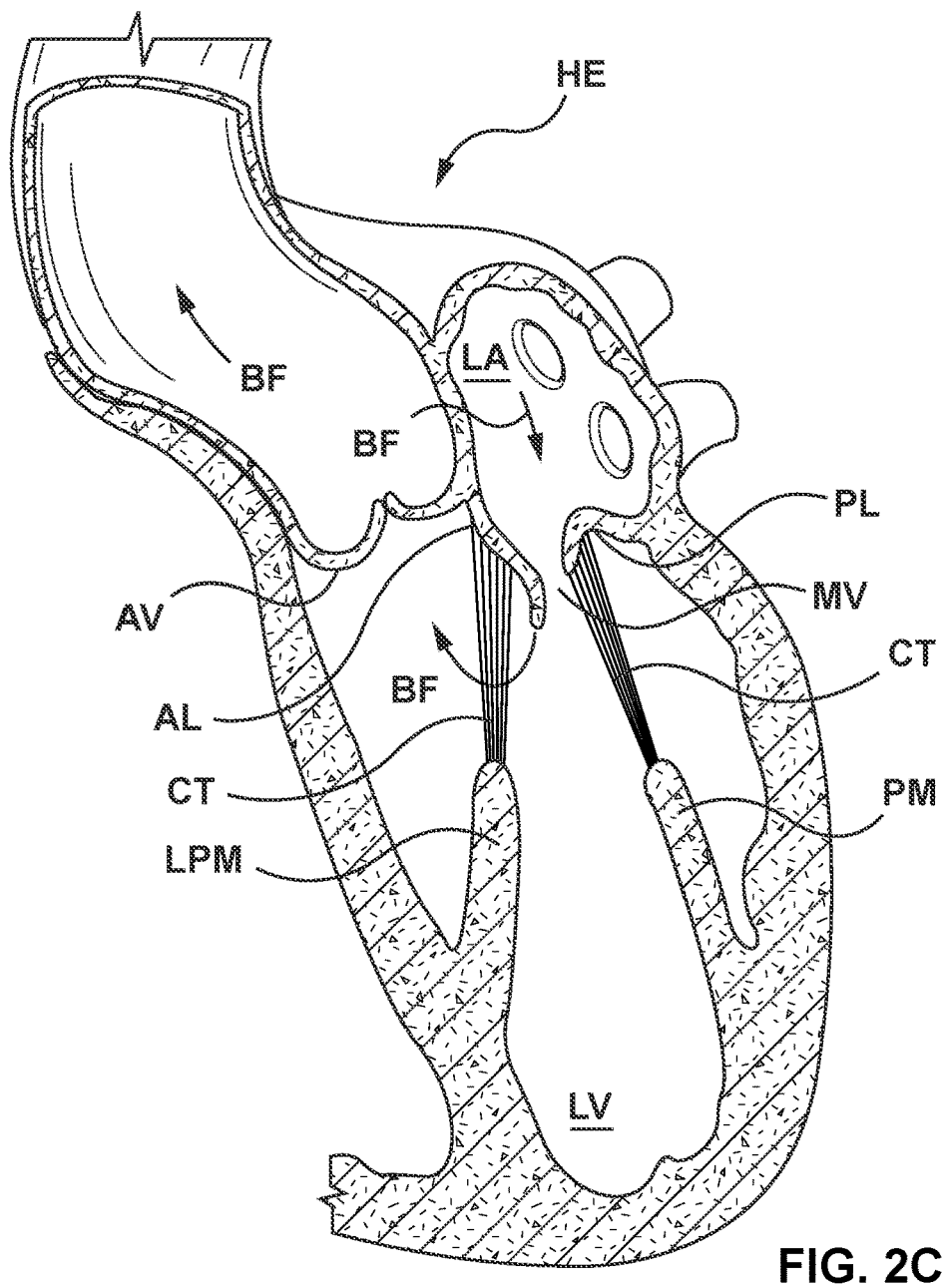
FIG. 2C is a schematic sectional illustration of the left ventricle of FIG. 2B as viewed from a different angle.
Figure 2D:
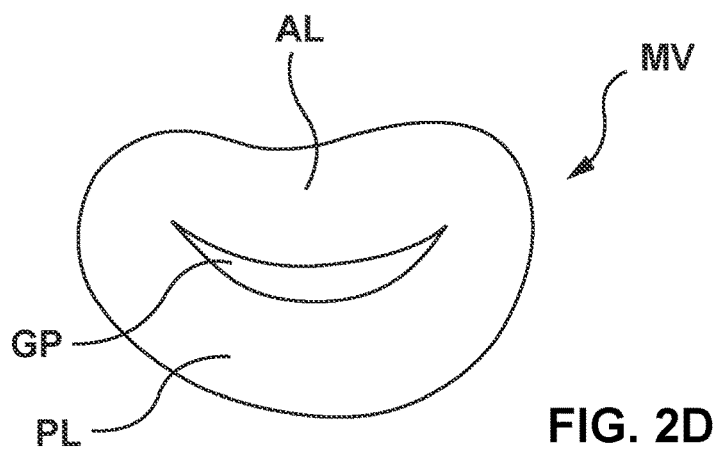
FIG. 2D is a top view illustration of the prolapsed mitral valve of FIG. 2B, wherein the mitral valve is in an open configuration.

FIGS. 1-2D will now be described to provide contextual information on valve regurgitation. FIG. 1 is a schematic sectional illustration of a mammalian heart HE that depicts the four heart chambers (right atrium RA, right ventricle RV, left atrium LA, left ventricle LV) and native valve structures (tricuspid valve TV, mitral valve MV, pulmonary valve PV, aortic valve AV). FIG. 2A is a schematic sectional illustration of a left ventricle LV of a mammalian heart HE showing anatomical structures and a native mitral valve MV. Referring to FIGS. 1 and 2A together, the heart HE comprises the left atrium LA that receives oxygenated blood from the lungs via the pulmonary veins. The left atrium LA pumps the oxygenated blood through the mitral valve MV and into the left ventricle LV during ventricular diastole. The left ventricle LV contracts during systole and blood flows outwardly through the aortic valve AV, into the aorta and to the remainder of the body.

In a healthy heart, the mitral valve MV includes an open configuration and a closed configuration. When the mitral valve MV is in the open configuration, an anterior leaflet AL and a posterior leaflet PL do not coapt, permitting blood to flow from the right atrium RA to the left ventricle LV. When the mitral valve is in the closed configuration, as shown in FIG. 2A, the anterior and posterior leaflets AL, PL of the native mitral valve MV meet evenly at the free edges or "coapt" to close and prevent back flow of blood into the left atrium LA during contraction of the left ventricle LV. The tissue of the anterior and posterior leaflets AL, PL attach to the surrounding heart structure via a dense fibrous ring of connective tissue called an annulus AN which is distinct from both the tissue of the anterior and posterior leaflets AL, PL as well as the adjoining muscular tissue of the heart wall. In general, the connective tissue at the annulus AN is more fibrous, tougher and stronger than leaflet tissue. The flexible tissue of the anterior and posterior leaflets AL, PL of the native mitral valve MV are connected to papillary muscles PM, which extend upwardly from the lower wall of the left ventricle LV and the interventricular septum IVS, via branching tendons called chordae tendinae CT.

In a heart HE having a mitral valve MV experiencing valvular regurgitation due to a prolapsing first or posterior leaflet PL and a second or anterior leaflet AL, the respective edges of the posterior leaflet PL and the anterior leaflet AL do not sufficiently coapt or meet, as shown in FIGS. 2B-2D and leakage from the left ventricle LV into the left atrium LA will occur through a gap GP. Several structural defects can cause the mitral leaflets LF to prolapse, and subsequent regurgitation to occur, including ruptured chordae tendinae CT, impairment of papillary muscles PM (e.g., due to ischemic heart disease), and enlargement of the heart and/or mitral valve annulus AN (e.g., cardiomyopathy).

Embodiments of systems and associated methods in accordance with the present technology are described with reference to FIGS. 3A-14. It will be appreciated that specific elements, substructures, uses, advantages, and/or other aspects of the embodiments described herein and with reference to FIGS. 3A-14 can be suitably interchanged, substituted or otherwise configured with one another in accordance with additional embodiments of the present technology.

Provided herein are systems and methods suitable for repairing a prolapsing leaflet of a heart valve to reduce or eliminate valvular regurgitation. More specifically, in embodiments hereof, a flexible canopy of the system is placed over an existing native leaflet of the heart valve and tensioned with an elongated tether to prevent leaflet prolapse and subsequent regurgitation resulting from the prolapsing leaflet. The system is adjustable via the elongated tether to set the system to minimize or eliminate valvular regurgitation. Further, the system may be readjusted during the initial procedure or in a subsequent procedure or procedures to account for changes in the native anatomy over time. The systems described herein do not reduce or alter the cross-sectional area of the native mitral valve and thus reduced blood flow through the heart valve is avoided and easy access to the heart valve is still permitted for future therapies and treatments.

Figure 3A:
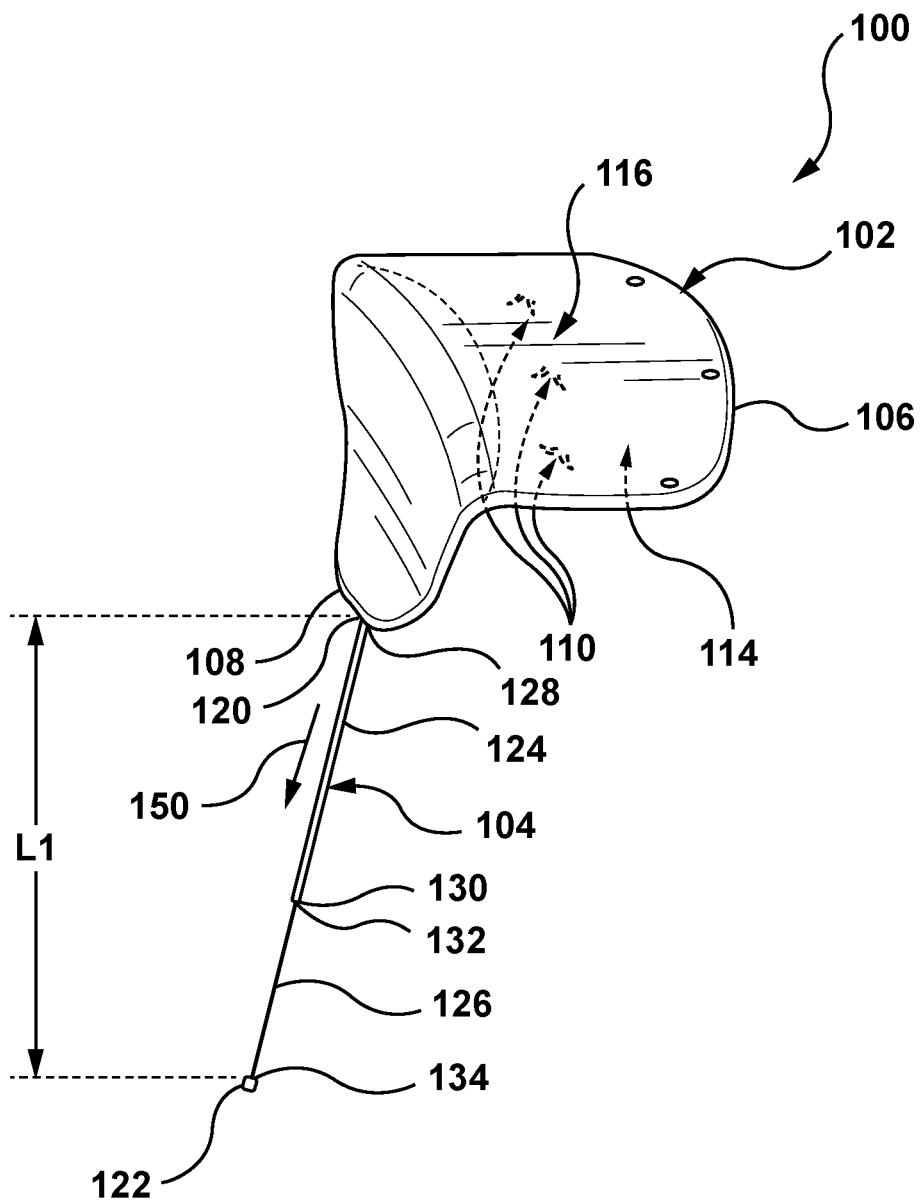
FIG. 3A is a perspective illustration of a system for treating heart valvular regurgitation in accordance with an embodiment hereof.

Turning now to FIG. 3A, FIG. 3A is a perspective view of a system 100 for treating valvular regurgitation in a heart valve due to a prolapsing leaflet and configured in accordance with an embodiment hereof. The system 100 includes a flexible canopy 102 and an elongated tether 104. Further, the system 100 includes a delivery configuration, wherein the system is compressed for percutaneous delivery within a delivery catheter to a desired treatment location, and a deployed configuration, which is shown in FIG. 3A. When the system 100 is in the delivery configuration, the flexible canopy 102 can be folded, rolled, or otherwise compressed. The method of compressing the flexible canopy 102 is selected based upon a variety of characteristics including, but not limited to the order or sequence of anchor fixation or deployment.

Figure 3B:
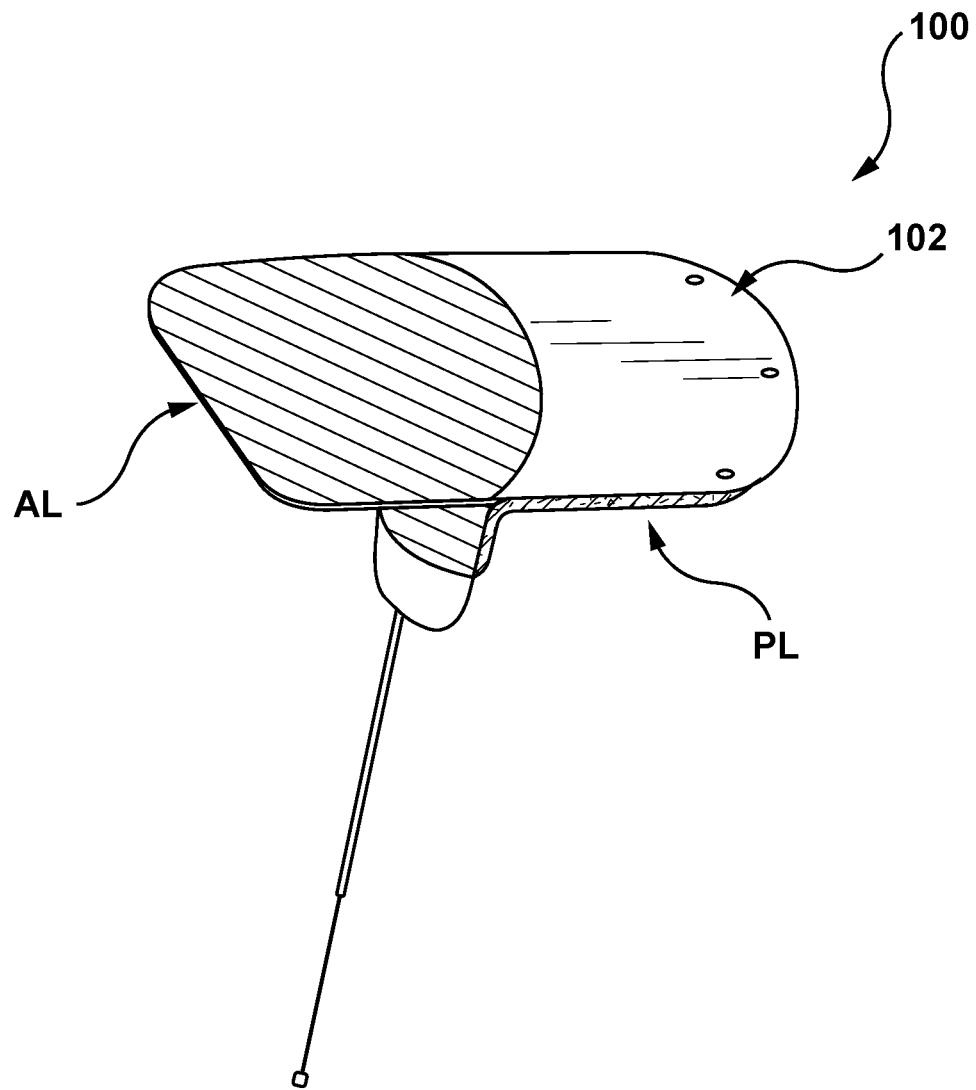
FIG. 3B is a perspective illustration of the system of FIG. 3A and an anterior leaflet of a native mitral valve.

As shown in FIG. 3A, the flexible canopy 102 is formed of a flexible material and includes a proximal end 106, a distal end 108 opposite the proximal end 106, an underside or first surface 114 and a top or second surface 116 opposite the first surface 114. The flexible canopy 102 may be formed of materials which will bond to the prolapsing leaflet via growth such as, but not limited to Dacron®, pericardial tissue, or other suitable materials. The proximal end 106 of the flexible canopy 102 is configured to be anchored in situ at or on an annulus of the heart valve. As used herein, "at or on" an annulus means at or on a level of a plane of the annulus of the native heart valve, including disposition at or on a level of an upper surface of the annulus or other superior levels of the valve. Further, when the system 100 is in the deployed configuration, the flexible canopy 102 is configured to overlay an underlying or concealed portion of a prolapsing leaflet of the native heart valve such that the first surface 114 abuts against or contacts the underlying portion of the prolapsing leaflet, as described in more detail below. The flexible nature of the flexible canopy 102 permits the flexible canopy 102 to conform to the shape of the native prolapsing leaflet as best shown in FIG. 3B. FIG. 3B shows the system 100 with the flexible canopy 102 thereof overlaying and conforming to a native posterior leaflet PL, with the flexible canopy 102 coapting with a native anterior leaflet AL of a native heart valve. As used herein, the term "conform" means that the flexible canopy 102 assumes the same shape, outline, or contour of the underlying anatomy of the native prolapsing leaflet such that the flexible canopy 102 maintains consistent and close contact with the native prolapsing leaflet adjacent thereto. Thus, while the flexible canopy 102 of FIG. 3A is shown with a particular shape, this is by way of example and not limitation, and it will be understood that the flexible canopy 102 assumes or conforms to the shape of the native prolapsing leaflet. Such conformability is required in order for the system 100, and more particularly the flexible canopy 102 to prevent the native leaflet from prolapsing when the system 100 is in the deployed configuration as described in greater detail below. Over time, due to the material of the flexible canopy 102, the first surface 114 of the flexible canopy 102 bonds or fuses to the underlying first surface of the prolapsing leaflet.

In the embodiment of FIG. 3A, the first surface 114 of the flexible canopy 102 includes a plurality of micro-tines or micro-barbs 110 configured to aid in coupling the first surface 114 of the flexible canopy 102 to the underlying first surface of the native prolapsing leaflet. While shown in FIG. 3A with three (3) micro-barbs 110, this is by way of example and not limitation and more or fewer micro-barbs 110 may be used. In an embodiment, the micro-barbs 110 may have a diameter in a range of between about 0.005 inches and about 0.010 inches, and the length of the micro-barbs 110 may be in a range of between about 0.010 inches and about 0.100 inches. The micro-barbs 110 may be shaped to embed into an adjacent surface such as, but not limited to, a wedged shape where the tip of the wedge comes in contact with the adjacent surface. In another embodiment, the micro-barbs 110 may be a series of metallic wires.

In the embodiment depicted in FIGS. 3A and 3B, the flexible canopy 102 is unsupported. Stated another way, in the embodiment depicted in FIGS. 3A and 3B, the flexible canopy 102 does not include a support frame and consists only of the flexible material that has the first surface 114 and the opposing second surface 116. As used herein, "unsupported" means that the flexible canopy has no radial or longitudinal support along its length and is not attached to a scaffold or frame structure. Due to the unsupported nature thereof, the flexible canopy 102 is permitted to conform to the underlying leaflet structure and further is non-traumatic to the surrounding native anatomy.

The size and perimeter of the flexible canopy 102 may be selected based upon the desired amount of leaflet coverage, the shape of the native anatomy, and/or desired anchoring positions. As best shown in FIG. 3B, in an embodiment hereof, the flexible canopy 102 has an oblong shape and is configured to overlay the prolapsing leaflet of the native heart valve such that the first surface 114 of the flexible canopy is in contact with substantially the entire underlying surface (i.e., at least 90%) of the prolapsing leaflet of the native heart valve. In another embodiment hereof, the flexible canopy 102 is configured to overlay the prolapsing leaflet of the native heart valve such that the first surface 114 of the flexible canopy is in contact with between forty and ninety percent (40-90%) of the underlying surface of the prolapsing leaflet of the native heart valve. In addition, while the flexible canopy 102 of FIGS. 3A and 3B is shown with a particular length that extends distally a particular distance, this is by way of example and not limitation, and it will be understood that other lengths that are suitable to treat valvular regurgitation may be used. More particularly, as best shown in FIG. 3B, in an embodiment the flexible canopy 102 extends distally beyond a distal end of the native posterior leaflet PL. However, in an alternative embodiment, the flexible canopy 102 does not extend beyond a prolapsing portion of the posterior leaflet PL. It will be understood that the shape and size of the flexible canopy 102 may assume any and all possible permutations including, but not limited to the flexible canopy 102 spanning most of the native prolapsing leaflet, spanning just past the prolapsing portion of the native prolapsing leaflet or any other configurations suitable for the purposes described herein.

The elongated tether 104 will now be described in more detail with reference to FIG. 3A. The elongated tether 104 has a first length L1 extending from a proximal end 120 thereof, which is attached to the distal end 108 of the flexible canopy 102, to a distal end 122 thereof. The proximal end 120 of the elongated tether 104 may be coupled to the distal end 108 of the flexible canopy 102 by methods including but not limited to adhesives, tying, sutures, mechanical devices, fusing, or any other method suitable for the purposes described herein. The elongated tether 104 includes an elastic portion 124 coupled to an inelastic portion 126. The elastic portion 124 is an elongate member having elastic qualities. As used herein, "elastic" means that the elongate member returns or is able to resume its original length or shape after distortion. The elastic portion 124 may be formed of elastic materials such as, but not limited to prosthetic chordae materials such as silicone, gore, Gore-tex®, or any other suitable material. When the system 100 is in the deployed configuration in situ, the elastic portion 124 is configured to allow for dynamic movement of the flexible canopy 102. The inelastic portion 126 is an elongate member having inelastic qualities. As used herein, "inelastic" means that the elongate member 126 is not elastic and cannot be stretched. The inelastic portion 126 may be formed of inelastic materials such as, but not limited to a monofilament or plastic suture materials such as polypropylene, metal alloys such as stainless steel, titanium, or nickel-titanium alloys (i.e. NITINOL), or any other suitable material.

The elongated tether 104 is continuous or stated another way, the elastic portion 124 and the inelastic portion 126 collectively form the elongated tether 104. The elastic portion 124 includes a proximal end 128 and a distal end 130, while the inelastic portion 126 includes a proximal end 132 and a distal end 134. In the embodiment of FIGS. 3-6, the elastic portion 124 is disposed proximal of the inelastic portion 126. More specifically, the proximal end 128 of the elastic portion 124 is coupled to the distal end 108 of the flexible canopy 102 and the distal end 130 of the elastic portion 124 is coupled to the proximal end 132 of the inelastic portion 126. The proximal end 132 of the inelastic portion 126 may be coupled to the distal end 130 of the elastic portion 124 by methods including, but not limited to adhesives, tying, sutures, mechanical devices, fusing, or any other method suitable for the purposes described herein. The ratio of the elastic portion 124 to the inelastic portion 126 with reference to the first length L1 of the elongated tether 104 is selected based on a variety of characteristics including, but not limited to the native valve location, the native anatomy, and the characteristics and geometry of the system 100. In an embodiment hereof, as shown in FIGS. 3A and 3B, the elastic portion 124 is longer than the inelastic portion 126 to ensure that dynamic movement of the flexible canopy 102 is permitted in situ. For example, the ratio of the elastic portion 124 to the inelastic portion 126 of the elongated tether 104 may be 50/50, 60/40, 70/30, or other ratio found suitable for repairing valvular regurgitation.

The distal end 122 of the elongated tether 104 is coupled to a distal anchor (not shown in FIG. 3A) which is anchored in a ventricle adjacent the prolapsing valve. The elongated tether 104 is configured to be placed into tension when the system 100 is in the deployed configuration and implanted in situ, as described in more detail below. When placed into tension, the elongated tether 104 pulls on the distal end 108 of the flexible canopy 102 in a distal direction as indicated by a directional arrow 150. Stated another way, when the elongated tether 104 is placed into tension during implantation, the elongated tether 104 places the flexible canopy 102 into tension. Further, the tension on the elongated tether 104 is configured to be adjustable in situ to adjust or tune the curvature of the flexible canopy 102 and/or the angle at which the flexible canopy 102 coapts with the non-prolapsing leaflet or leaflets of the heart valve to minimize or reduce regurgitation. When the tension applied to the elongated tether 104 is increased, the elastic portion 124 of the elongated tether 104 stretches or elongates and the first length L1 of the elongated tether 104 relatively increases. Conversely, when the tension applied to the elongated tether 104 is decreased, the elastic portion 124 of the elongated tether 104 shortens and the first length L1 of the elongated tether 104 relatively decreases. Devices and methods for placing the elongated tether 104 into tension will be discussed in more detail with respect to FIG. 4 below.

Figure 4:
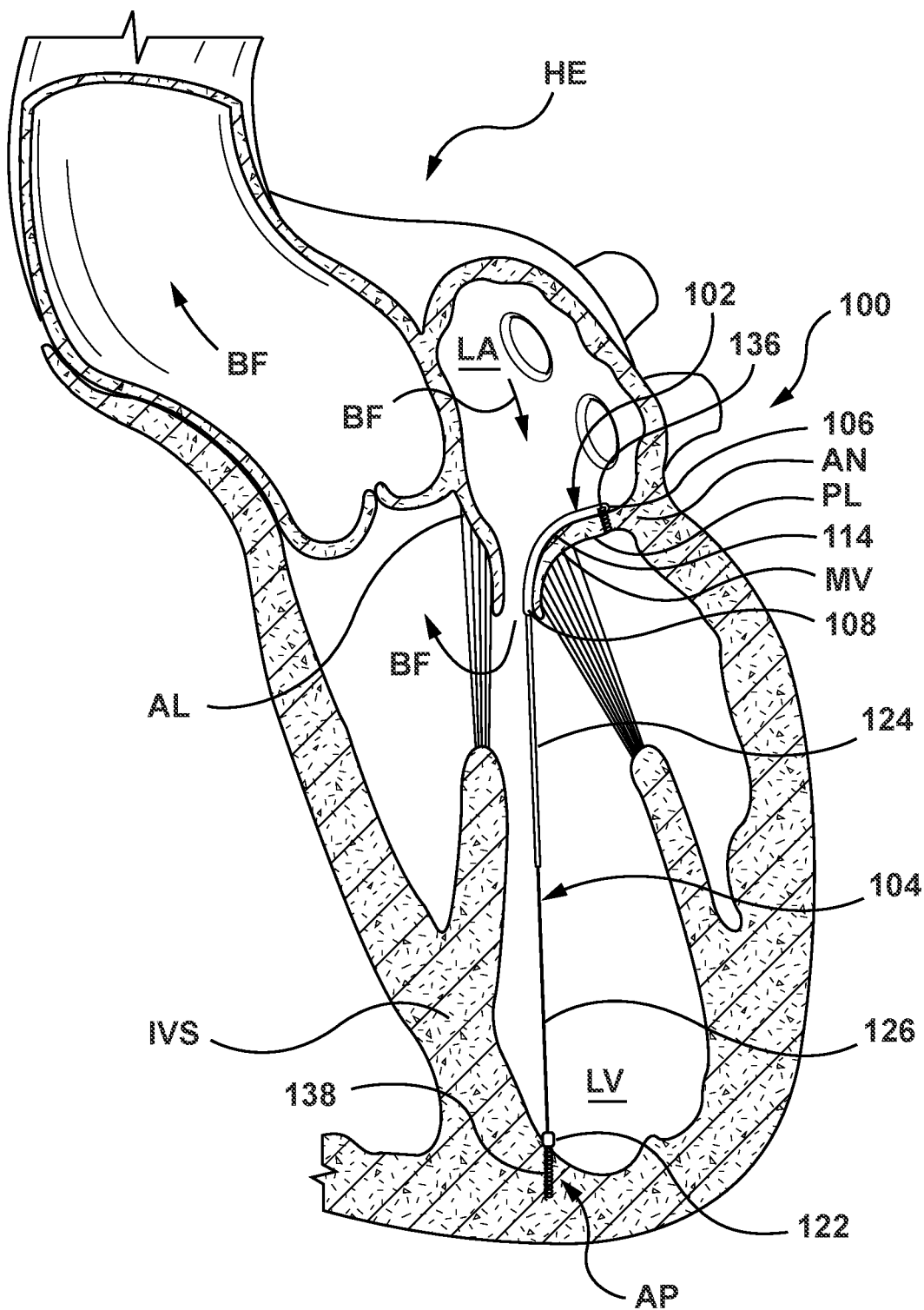
FIG. 4 is a schematic sectional illustration of a heart, wherein the system of FIG. 3A is implanted within the heart in a deployed configuration and a native mitral valve of the heart is in the open configuration.
Figure 5:
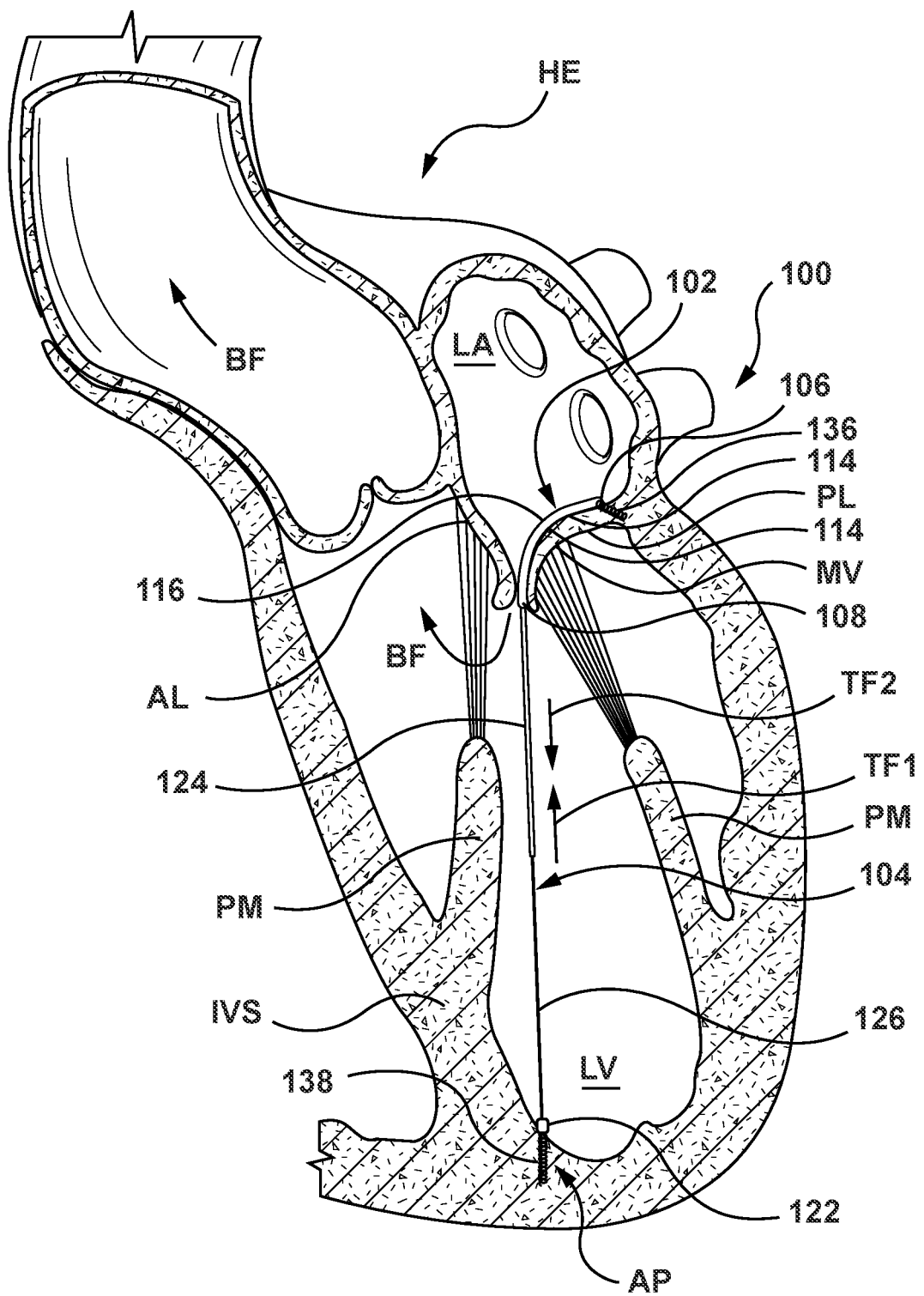
FIG. 5 is a schematic sectional illustration of the heart, wherein the system of FIG. 3A is implanted within the heart in a deployed configuration and the native mitral valve of the heart in a closed configuration.
Figure 6:
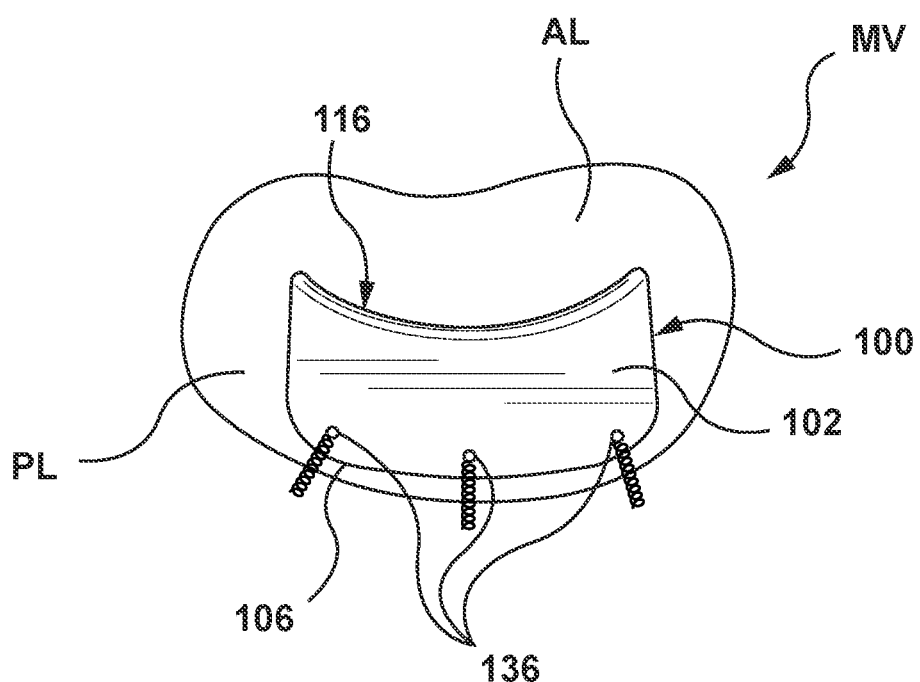
FIG. 6 is a top view illustration of the mitral valve of FIG. 5, wherein the mitral valve is in the closed configuration.

The interaction of the components of the system 100 will now be described with reference to FIGS. 4-6. FIGS. 4 and 5 are schematic sectional illustrations of the system 100 in a deployed configuration implanted within a heart HE, with FIG. 4 illustrating a native mitral valve MV of the heart in an open configuration and FIG. 5 illustrating the native mitral valve MV of the heart HE in a closed configuration. FIG. 6 is a top view illustration of the native mitral valve MV of the heart HE in the closed configuration. Within FIGS. 4-6, the direction of blood flow is indicated by arrows BF. The system 100 is configured to repair a prolapsing posterior leaflet PL of the mitral valve MV. More particularly, when the system 100 is in the deployed configuration and implanted within the heart HE, the proximal end 106 of the flexible canopy 102 is anchored or coupled to an annulus AN of the mitral valve MV by at least one proximal anchor 136. The first surface 114 of the flexible canopy 102 overlays and is in contact with an underlying first surface of the first or posterior leaflet PL of the mitral valve MV. The elongated tether 104 extends from the distal end 108 of the flexible canopy 102 to a distal anchor 138 in the left ventricle LV.

The proximal and distal anchors 136, 138 may be of any anchor suitable for embedding into the tissue of the annulus AN and the left ventricle LV, respectively, including but not limited to helical screws or anchors, barbs, or clips. In the embodiment illustrated in FIGS. 4 and 5, each of the proximal anchors 136 and the distal anchor 138 are shown as helical screws or anchors. Each helical anchor 136, 138 is rotatable by a corresponding releasable shaft of a delivery catheter to embed the respective helical anchor in myocardial tissue. For example, and not by way of limitation, each of the proximal and distal anchors 136, 138 may be an anchor as described in U.S. Pat. No. 3,974,834 to Kane or U.S. Pat. No. 4,046,151 to Rose, each of which is assigned to the same assignee of the present invention and each of which is hereby incorporated by reference in its entirety herein. While described herein as helical anchors 136, 138, this is by way of example and not limitation and the shape of the proximal and distal anchors 136, 138 may have other shapes and other methods for delivery. For example, and not by way of limitation, the proximal and/or distal anchors 136, 138 may be an anchor as described in U.S. Pat. No. 4,341,226 to Peters or U.S. Pat. No. 9,775,982 to Grubac et al., each of which is assigned to the same assignee of the present invention and each of which is hereby incorporated by reference in its entirety herein.

As described above, when the system 100 is in the deployed configuration and implanted in situ as shown in FIG. 4, the elongated tether 104 is placed into tension in order to properly position the flexible canopy 102 to overlay the underlying first surface of the first or posterior leaflet PL of the mitral valve MV. In an embodiment hereof, the distal end 122 of the elongated tether 104 is pre-attached to the distal anchor 138 and the elongated tether 104 is placed into tension by attaching the distal anchor 138 to the left ventricle LV in such a way that provides tension to the elongated tether 104. More particularly, tension is provided to the elongated tether 104 by varying the amount that the distal anchor 138 is advanced or embedded into a wall of the left ventricle LV. For example, when the distal anchor 138 is a helical screw as shown, the distal anchor 138 may be screwed into the wall of the left ventricle LV a greater amount or distance to increase the tension applied to the elongated tether 104. Conversely, the distal anchor 138 may be unscrewed to decrease the tension applied to the elongated tether 104, if desired. In another embodiment hereof, the distal end 122 of the elongated tether 104 is pre-attached to the distal anchor 138, and the elongated tether 104 is placed into tension by varying the angle at which the elongated tether 104 extends from the flexible canopy 102. More particularly, the location of the distal anchor 138 may be moved to increase or decrease the angle at which the elongated tether 104 extends from the flexible canopy 102. For example, the location of the distal anchor 138 may be moved towards the apex AP of the left ventricle LV to increase the tension applied to the elongated tether 104. Conversely, the location of the distal anchor 138 may be moved towards the interventricular septum IVS of the left ventricle LV to decrease the tension applied to the elongated tether 104.

In another embodiment hereof, the elongated tether 104 is configured to be placed into tension via a tensioning device or tensioner (now shown). For example, a tensioning device as described in U.S. Pat. No. 9,452,048 to O'Bierne et al., assigned to the same assignee of the present invention and which is hereby incorporated by reference in its entirety herein, may be modified and utilized as a tensioning device or tensioner. For example, the elongated tether 104 may initially be slidably coupled to the distal anchor 138 via an integral loop of the elongated tether 104 such that a free end of the elongated tether 104 extends proximally through a delivery catheter and is accessible to the physician. After the distal anchor 138 is secured to the wall of the ventricle, the physician may pull on the accessible free end of the elongated tether 104 to effectively decrease the first length L1 of the elongated tether 104 in situ and further effectively increase the tension placed on the elongated tether 104. Conversely, the physician may release or push the free end of the elongated tether 104 to effectively increase the first length L1 of the elongated tether 104 in situ and further effectively decrease the tension placed the elongated tether 104. Once the tension is optimized, a locking mechanism as described in U.S. Pat. No. 9,452,048 to O'Bierne et al., previously incorporated by reference above, may be slid or advanced over the free end of the elongated tether 104 and through the delivery catheter until the locking mechanism abuts against the distal anchor 138 and thereby secures the position of the elongated tether 104 being placed under the desired amount of tension. Any excess length of the elongated tether 104, i.e., the length of tether extending from the locking mechanism to the free end extending proximally back to the physician, may be cut and removed from the patient. A tensioning device has been described herein by way of example and not limitation. It will be understood that the tensioning device may be any suitable device configured to permit the elongated tether 104 to be placed into tension, and more specifically to adjust or change the first length L1 of the elongated tether 104 to increase or decrease the amount of tension placed onto the elongated tether 104 as described above.

Regardless of which method or device is used to place the elongated tether 104 into tension, the first length L1 of the elongated tether 104 is varied during adjustment of the tension placed on the elongated tether 104. Accordingly, when the first length L1 of the elongated tether 104 is reduced to increase the tension placed on the elongated tether 104, the elastic portion 124 thereof is stretched. Because of the desire of the elastic portion 124 to return to its resting shape or length, the elastic portion 124 is placed into spring tension. This spring tension is transferred to adjacent coupled components as a tension force. More precisely, the spring tension pulls on the proximal end 132 of the inelastic portion 126 and is transferred through the inelastic portion 126 to the distal end 122 of the elongated tether 104 anchored to the left ventricle LV by the distal anchor 138 with a first tension force represented by a directional arrow TF1 illustrated in FIG. 5. Further, the spring tension pulls on the distal end 108 of the flexible canopy 102 and is transferred through the flexible canopy 102 to the proximal end 106 of the flexible canopy 102 anchored at the annulus AN by the at least one proximal anchor 136 with a second tension force represented by a directional arrow TF2 illustrated in FIG. 5. For the purposes described herein, the distal anchor 138 and the at least one proximal anchor 136 are stationary relative to the system 100. It will be understood that the first and second tension forces TF1 and TF2 are equal and opposite. The distal end 108 of the flexible canopy 102 is pulled in the direction of the arrow TF2 with sufficient tension force that the flexible canopy 102, or more precisely the first surface 114 thereof is placed into contact with the underlying first surface of the posterior leaflet PL, and thereby prevents the posterior leaflet PL from prolapsing. Further, the tension force on the flexible canopy 102 may be adjusted to optimize coaptation of the flexible canopy 102 with the second leaflet of the heart valve, and to minimize valvular regurgitation. Stated another way, the tension force on the elongated tether 104 is adjustable to maximize coaptation of a portion of the second surface 116 of the flexible canopy 102 with an opposing mating portion of an anterior leaflet AL of the mitral valve MV, and to minimize or eliminate regurgitation at the mitral valve MV.

While shown with three proximal anchors 136 in specific locations in FIG. 6, this is by way of example and not limitation. It will be understood that more or fewer proximal anchors 136 may be used, and that the proximal anchor(s) 136 may be disposed at other locations. Further, while the distal anchor 138 is shown in FIG. 5 disposed at the apex AP of the left ventricle LV, this too is by way of example and not limitation. The distal anchor 138 may be disposed at any location within the left ventricle LV to optimize an angle between the coapting surfaces of the flexible canopy 102 and the anterior leaflet AL. For example, the distal anchor 138 may be disposed at any location within the left ventricle LV including, but not limited to the apex AP, the ventricle wall, the interventricular septum IVS, or the papillary muscle PM.

Figure 7A:
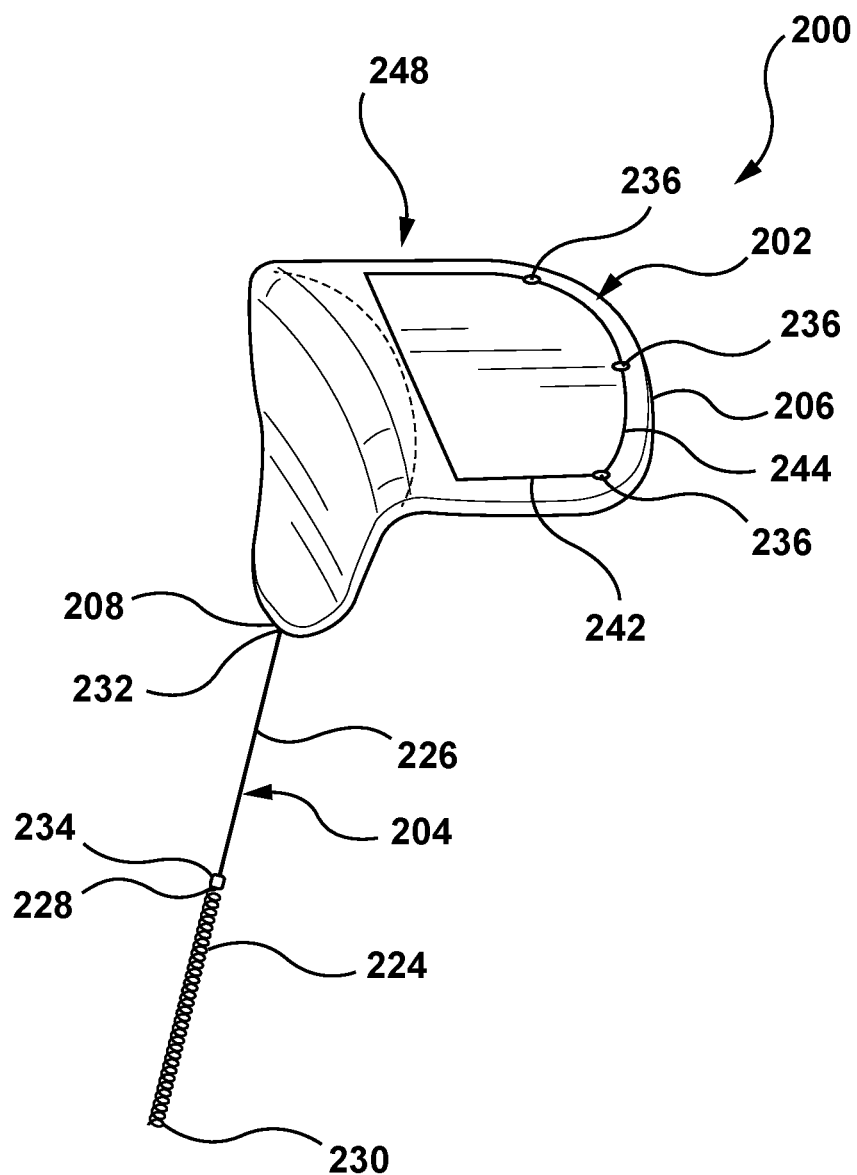
FIG. 7A is a perspective illustration of a system for treating heart valvular regurgitation in accordance with another embodiment hereof.

FIG. 7A is a perspective view of a system 200 for treating regurgitation of a heart valve due to a prolapsing leaflet and configured in accordance with another embodiment hereof. The system 200 includes a flexible canopy 202 and an elongated tether 204, the elongated tether 204 including an elastic portion 224 and an inelastic portion 226. In the embodiment in FIG. 7A, the flexible canopy 202 includes a frame 242 and the elongated tether 204 has an alternative configuration than the elongated tether 104 described above.

As shown in FIG. 7A, the flexible canopy 202 is formed of a flexible material and is similar to the flexible canopy 102 previously described. Therefore, similar details of the configuration and materials of the flexible canopy 202 will not be repeated. However, the flexible canopy 202 is supported by a frame 242 coupled to the material of the flexible canopy 202. The frame 242 is disposed at a proximal portion 248 of the flexible canopy 202. In the embodiment of FIG. 7A, the frame 242 has a D-shaped configuration and a first or curved end portion 244 of the frame 242 is disposed adjacent a proximal end 206 of the flexible canopy 202. The frame 242 is disposed adjacent to a perimeter of the flexible canopy 202 and the frame 242 further generally follows the shape of the perimeter of the flexible canopy 202. However, this is not meant to be limiting, and it will be understood that the frame 242 may be disposed at any location of the flexible canopy 202. In embodiments hereof, the frame 242 is configured to provide structural support to a proximal portion 248 of the flexible canopy 202. Further, the frame 242 serves to maintain coaptation angles between the flexible canopy 202 and the non-prolapsing leaflet or leaflets of the heart valve when the system 200 is in a deployed configuration and the heart valve is in a closed configuration. While shown with a specific shape, the frame 242 may have other shapes including but not limited to an ellipse, a circle, or any other shape suitable for the purposes described herein. Further, embodiments of the frame 242 may include additional struts or other strengthening members. The frame 242 may be formed of materials such as, but not limited to nickel titanium alloys (e.g. NITINOL), stainless steel, or other suitable materials. The frame 242 may be sewn into the flexible canopy 202 or may be coupled to the flexible canopy 202 by any other suitable method. In an embodiment, the frame 242 is attached to a plurality of proximal anchors 236.

In the embodiment of FIG. 7A, the frame 242 is configured to be disposed only on the atrial side of the native mitral valve when the system 200 is in a deployed configuration in situ. When the frame 242 is disposed only on the atrial side of the native mitral valve, the flexible canopy 202 is permitted to have increased flexibility within the left ventricle. Further, with the frame 242 disposed only on the atrial side of the native mitral valve, there are no relatively rigid or stiff elements of the frame 242 within the left ventricle LV that have potential to damage the chordae or other native anatomy within the left ventricle LV. In an alternate embodiment, the frame 242 may extend distally into the adjacent ventricle.

The elongated tether 204 of FIG. 7A is similar to the elongated tether 104 of FIG. 3A, except that the configuration or arrangement of the elastic and inelastic portions 224, 226, respectively are reversed from the configuration of the elongated tether 104 shown in FIG. 3A. More particularly, in the embodiment of FIG. 7A, the elastic portion 224 is disposed distal of the inelastic portion 226. The elastic portion 224 includes a proximal end 228 and a distal end 230. In the embodiment of FIG. 7A, the elastic portion 224 is a helical spring. As with the elastic portion 124 of FIG. 3A, the elastic portion 224 is configured to impart a tension force on the flexible canopy 202 as previously described with respect to the elastic portion 124 of FIG. 3A, and therefore is not described in detail with respect to FIG. 7A.

The configuration of the inelastic portion 226 of the elongated tether 204 of FIG. 7A includes a proximal end 232 coupled to the distal end 208 of the flexible canopy 202, a distal end 234 of the inelastic portion 226 coupled to the proximal end 228 of the elastic portion 224, and the distal end 230 of the elastic portion 224 coupled to the ventricle as previously described with respect to the distal end 134 of FIGS. 4-6. While the inelastic portion 226 and the elastic portion 224 are positioned at opposite ends of the elongated tether 204 than the elastic portion 124 and the inelastic portion 126 of the elongated tether 104 of FIG. 3A, it will be understood that applying and adjusting the tension force on the flexible canopy 202 is similarly accomplished by lengthening or shortening the length of the elongated tether 204.

Figure 7B:
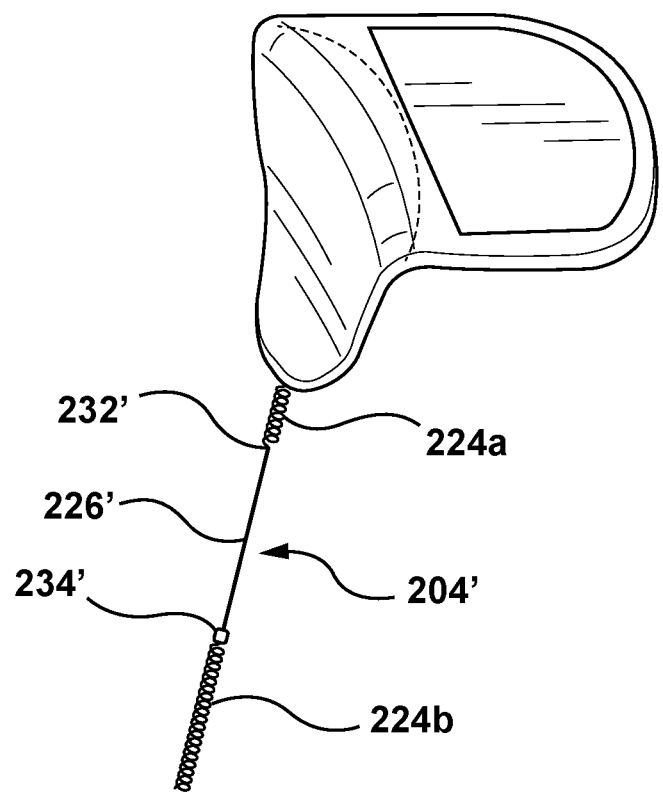
FIG. 7B is a perspective illustration of a system for treating heart valvular regurgitation in accordance with yet another embodiment hereof.

While described herein with one (1) spring elastic portion 224, in an alternative embodiment, an elongated tether 204' includes two (2) spring elastic portions 224a and 224b, disposed at the proximal end 232' and the distal end 234', respectively, of the inelastic portion 226', as shown in FIG. 7B. The two spring elastic portions 224a and 224b help to ensure that dynamic movement of the flexible canopy 202 is permitted in situ.

FIGS. 8-14 are sectional cut-away views of a heart HE illustrating method steps of treating regurgitation at a mitral valve MV via a transseptal approach for delivering and deploying the system 100 of FIG. 3 in accordance with an embodiment hereof. Access to the mitral valve MV can be accomplished through a patient's vasculature in a percutaneous manner. In an embodiment, the approach to the mitral valve is antegrade and may be accomplished via entry into the left atrium by crossing the interatrial septum. As is known in the art, a guidewire (not shown) may be advanced intravascularly using any number of techniques, e.g., through the inferior vena cava or superior vena cava (FIG. 1), into the right atrium RA through a penetration hole cut in the inter-atrial septum (not shown) and into the left atrium LA (FIG. 1). A guide catheter (not shown) may be advanced along the guidewire and into the right atrium RA, through the penetration hole in the inter-atrial septum, and into the left atrium LA. The guide catheter may have a pre-shaped or steerable distal end to shape or steer the guide catheter such that it will direct a delivery catheter toward the mitral valve MV.

Alternatively, the mitral valve may also be accessed via a transatrial approach for e.g., directly through an incision in the left atrium LA. Access to the heart may be obtained through an intercostal incision in the chest without removing ribs, and a guiding catheter (not shown) may be placed into the left atrium LA through an atrial incision sealed with a purse-string suture. A delivery catheter may then be advanced through the guiding catheter to the mitral valve. Alternatively, the delivery catheter may include a guidewire lumen such that it may be tracked over a guidewire and placed directly through the atrial incision without the use of a guiding catheter.

Figure 8:
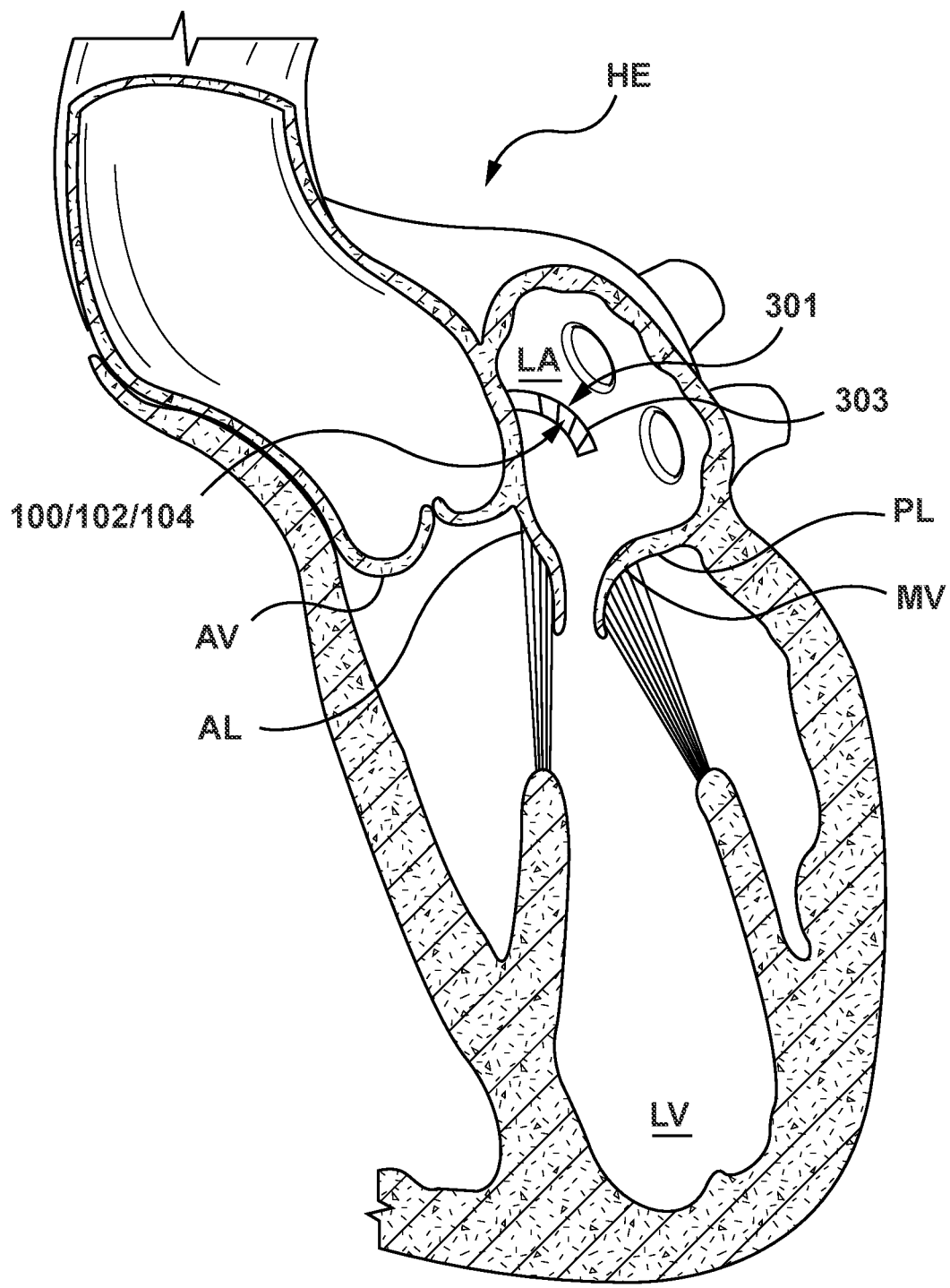
FIG. 8 is a sectional cut-away illustration of a heart illustrating a method step of using the system of FIG. 3A to repair a prolapsed posterior leaflet of a native mitral valve using a transseptal approach in accordance with an embodiment hereof, wherein the system of FIG. 3A is shown in the delivery configuration within a delivery catheter positioned within the left atrium of the heart.

Referring to FIG. 8, a distal segment 303 of a delivery catheter 301 is shown positioned in the left atrium LA. The delivery catheter 301 is delivered through the vasculature into the left atrium LA with the system 100 in a delivery configuration, in which the system 100 is radially compressed and disposed within the distal segment 303 of the delivery catheter 301. Intravascular access to the right atrium RA may be achieved via a percutaneous access site in a femoral, brachial, radial, or axillary artery. As will be understood by those knowledgeable in the art, a handle component (not visible in FIGS. 8-14), as well as some length of a proximal segment of the delivery catheter 301, are exposed externally of the patient for access by a clinician. By manipulating the handle of the delivery catheter 301 from outside the vasculature, a clinician may advance and remotely manipulate and steer the distal segment 303 of the delivery catheter 301 through the sometimes tortuous intravascular path. The distal segment 303 of the delivery catheter 301 may be distally advanced into the left atrium LA and positioned generally above (e.g., upstream) the mitral valve MV to deliver the system 100 to the mitral valve MV.

Figure 9:
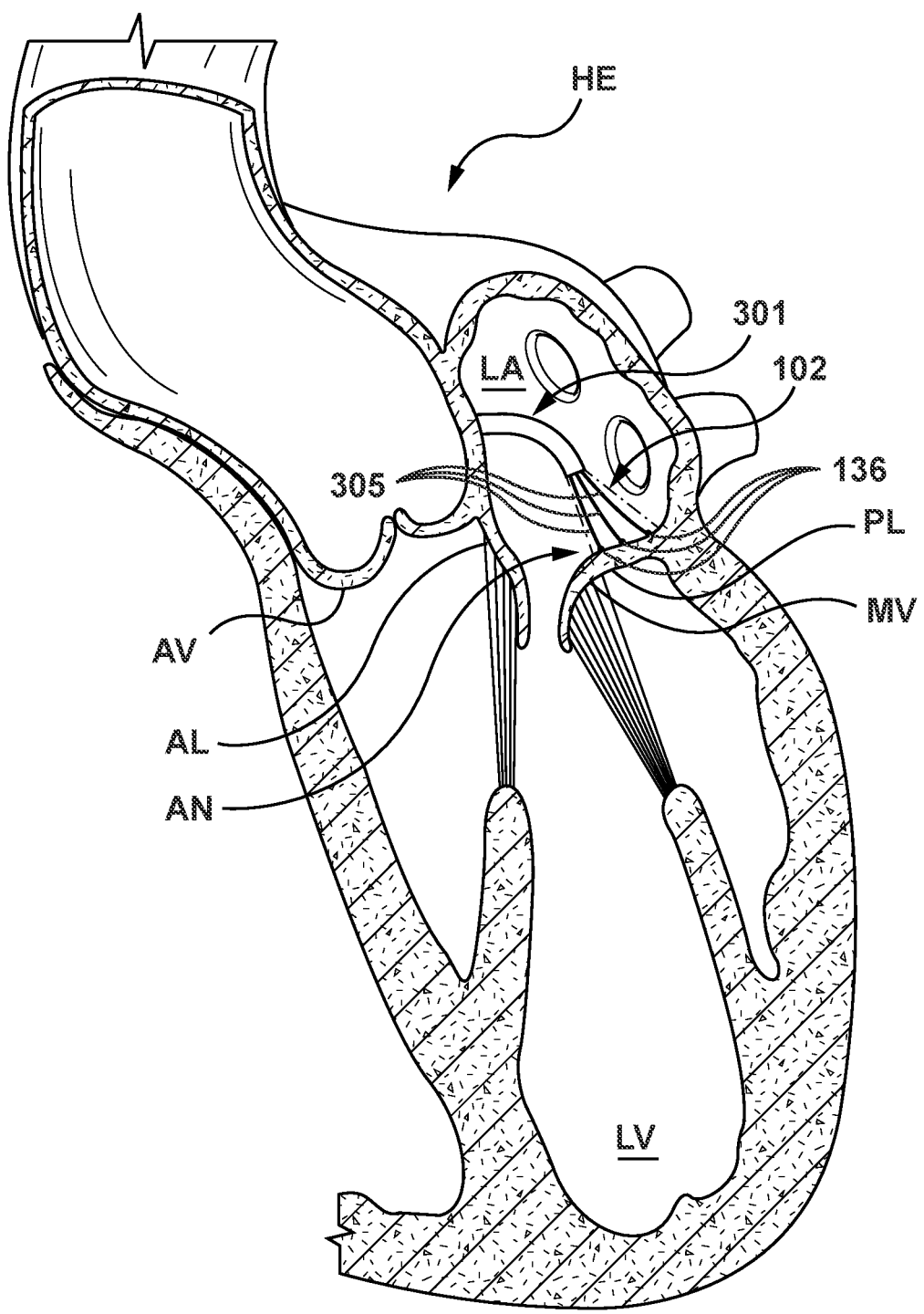
FIG. 9 is a sectional cut-away illustration of the heart illustrating a method step of using the system of FIG. 3A to repair the prolapsed posterior leaflet of the native mitral valve, wherein a plurality of proximal anchors is deployed to engage tissue at the annulus of the native mitral valve.

In a next delivery step shown in FIG. 9, three proximal anchors 136 are embedded in tissue at an annulus AN of the mitral valve MV. Embedding of each proximal anchor 136 at the annulus AN may be accomplished by various methods understood by those knowledgeable in the art. For example, and not by way of limitation, each proximal anchor 136 may be a helical anchor, rotated by a respective proximal anchor shaft 305 of the delivery catheter 301 to embed each proximal anchor 136 into tissue at the annulus AN. Each proximal anchor shaft 305 may be a shaft, rod, or lead as described, for example, in U.S. Pat. Nos. 3,974,834 or 4,046,151, each of which has previously been incorporated by reference in its entirety. Once each proximal anchor 136 is embedded at the annulus AN, the proximal anchor 136 is released from the respective proximal anchor shaft 305.

Figure 10:
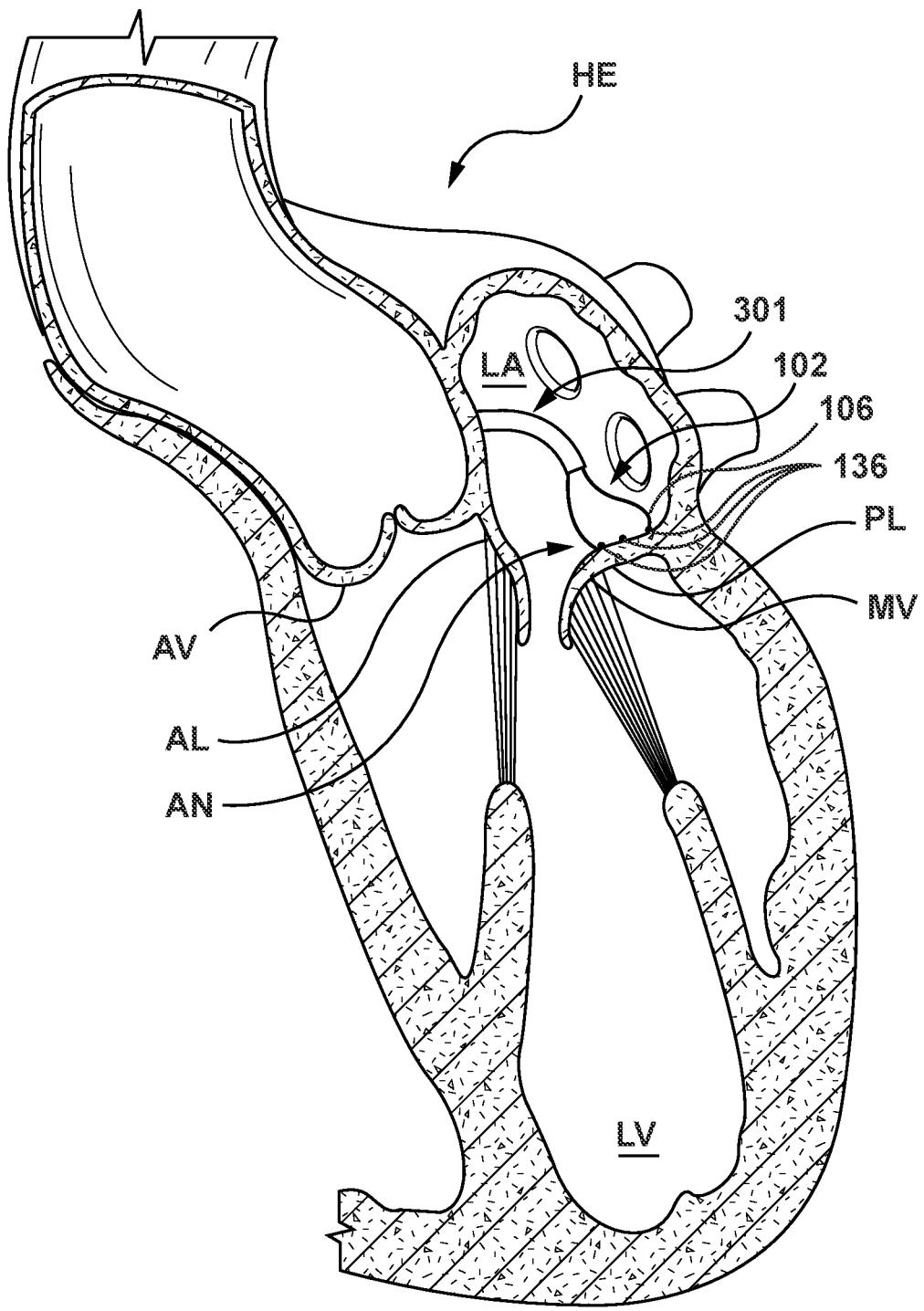
FIG. 10 is a sectional cut-away illustration of the heart illustrating a method step of using the system of FIG. 3A to repair the prolapsed posterior leaflet of the native mitral valve, wherein a proximal end of a flexible canopy of the system is coupled to the plurality of proximal anchors at the annulus of the native mitral valve.

In the embodiment of FIG. 9, each proximal anchor 136 is pre-attached to the flexible canopy 102 prior to delivery with the delivery catheter 301. Thus, once the proximal anchors 136 are embedded at the annulus AN and each proximal anchor 136 is released from the respective proximal anchor shaft 305, the proximal end 106 of the flexible canopy 102 remains attached to each of the proximal anchors 136 at the annulus AN, as shown in FIG. 10. The proximal end 106 is attached to the plurality of proximal anchors 136 to effectively anchor or secure the proximal end 106 of the flexible canopy 102 to the annulus AN of the native mitral valve MV.

While described herein with the flexible canopy 102 pre-attached to the plurality of proximal anchors 136 prior to delivery by the delivery catheter 301, this is by way of example and not limitation. It will be understood that the flexible canopy 102 can alternatively be coupled to the plurality of proximal anchors 136 after each of the proximal anchors 136 has been embedded at the annulus AN of the native mitral valve MV. For example, and not by way of limitation, the flexible canopy 102 may include a plurality of eyelets attached thereto with each proximal anchor shaft 305 disposed through a corresponding eyelet. The flexible canopy 102 can be deployed from the delivery catheter 301 by a push shaft or other device, and each eyelet and the flexible canopy 102 slide distally along the respective plurality of proximal anchor shafts 305 to couple to the corresponding proximal anchors 136. Once the flexible canopy 102 is coupled to the plurality of proximal anchors 136, each proximal anchor 136 is released by the respective proximal anchor shaft 305.

Figure 11:
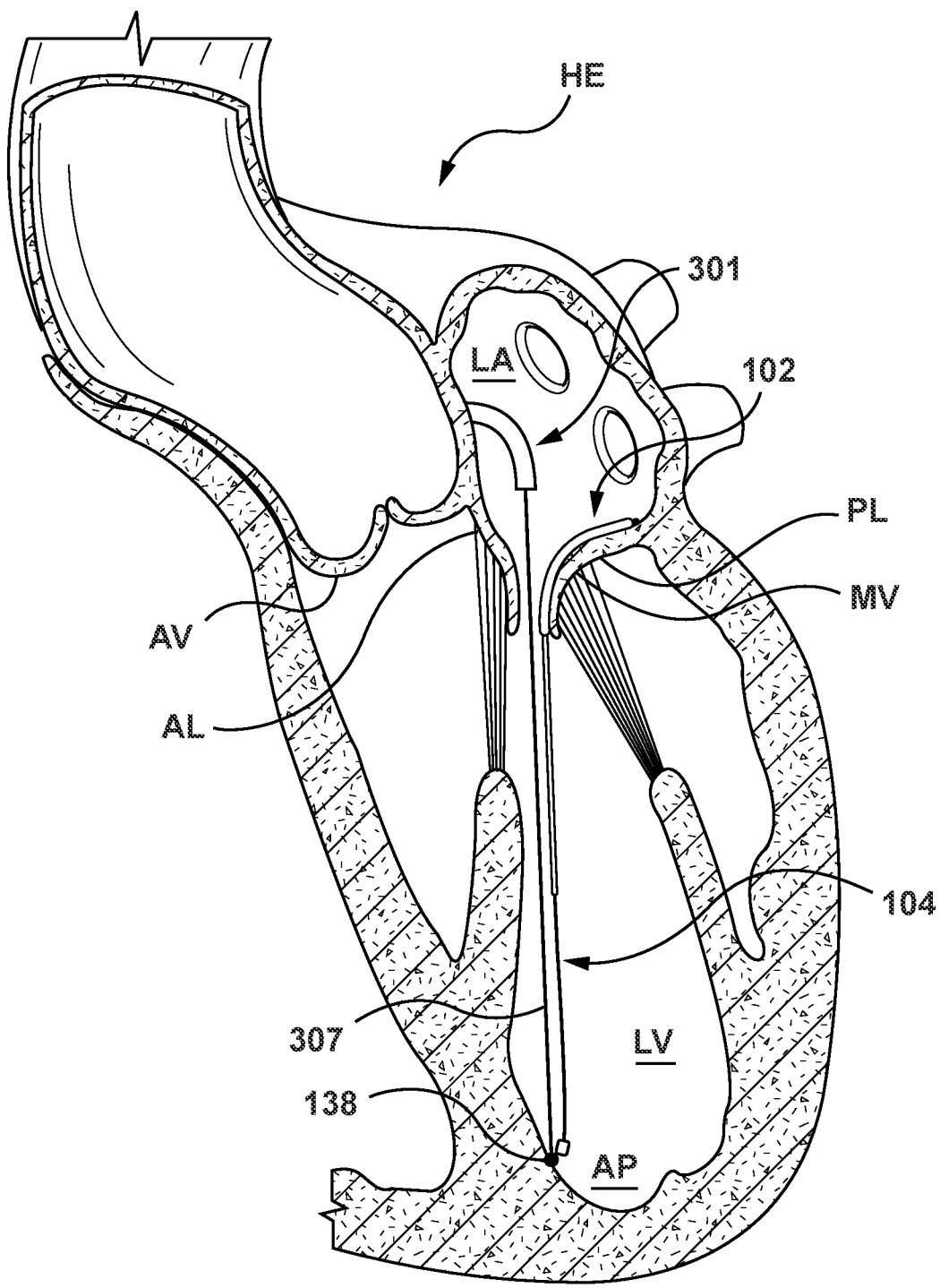
FIG. 11 is a sectional cut-away illustration of the heart illustrating a method step of using the system of FIG. 3A to repair the prolapsed posterior leaflet of the native mitral valve, wherein a distal anchor is deployed to engage tissue in a left ventricle of the heart.

As shown in FIG. 11, in a next step the distal anchor 138 is embedded in tissue within the left ventricle LV with a distal anchor shaft 307. Embedding of the distal anchor 138 may be accomplished by various methods understood by those knowledgeable in the art. For example, and not by way of limitation, the distal anchor 138 may be a helical anchor, rotated by the distal anchor shaft 307 to embed the distal anchor 138 in an apex AP of the left ventricle LV. The distal anchor shaft 307 may be a shaft, rod, or lead as described, for example, in U.S. Pat. Nos. 3,974,834 or 4,046,151 assigned to Medtronic, Inc., each of which has previously been incorporated by reference in its entirety. While shown with the distal anchor 138 embedded in tissue at an apex AP of the left ventricle LV, this is by way of example and not limitation. As previously described, the location of the distal anchor 138 within the left ventricle LV may be determined based upon the angle of the flexible canopy 102 in relation to the anterior leaflet AL to achieve optimal coaptation between the flexible canopy 102 and the anterior leaflet AL to minimize or eliminate regurgitation. Once the distal anchor 138 is embedded at the desired location of the left ventricle LV, the distal anchor 138 is released from the distal anchor shaft 307.

Figure 12:
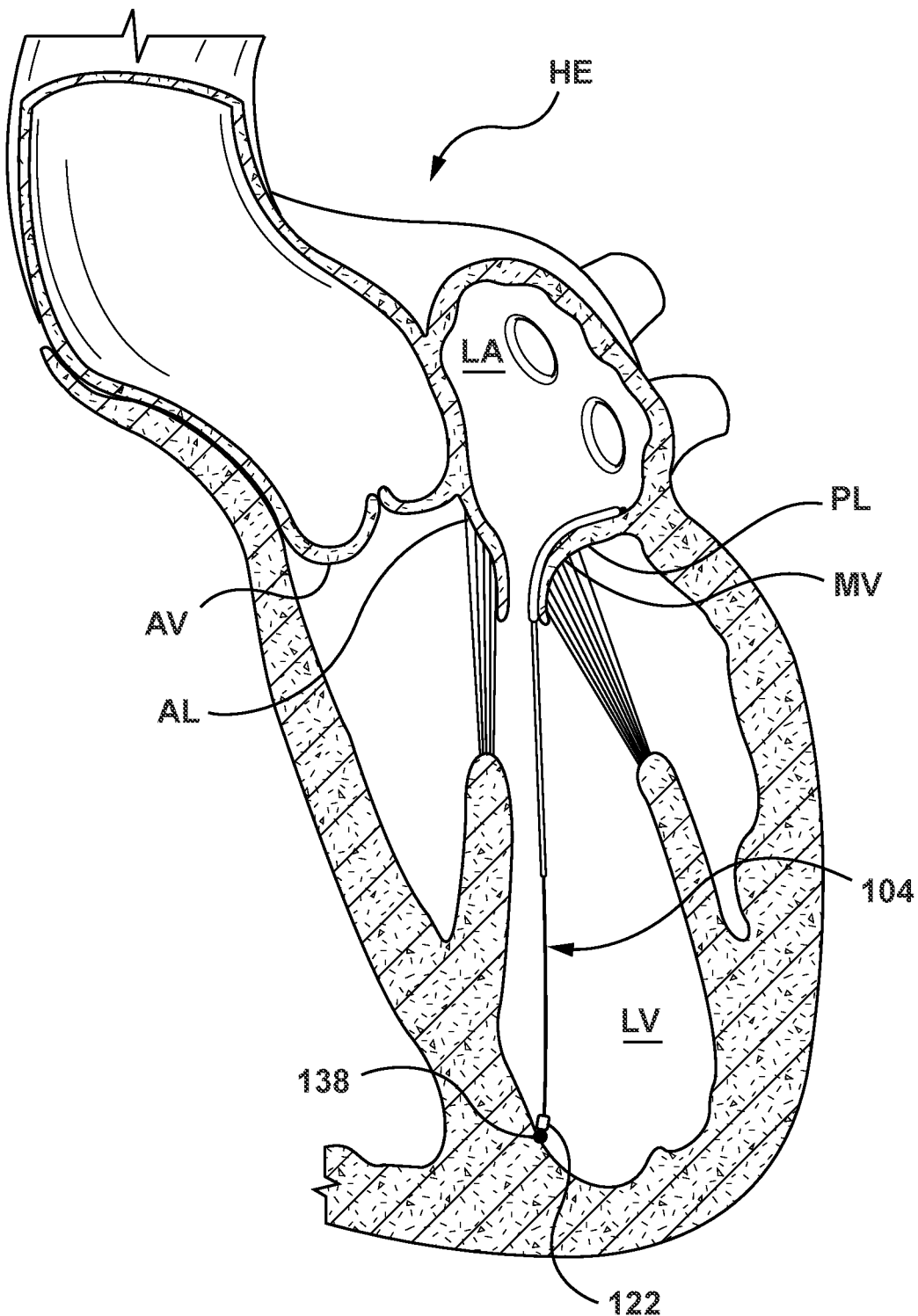
FIG. 12 is a sectional cut-away illustration of the heart illustrating a method step of using the system of FIG. 3A to repair the prolapsed posterior leaflet of the native mitral valve, wherein a distal end of an elongated tether of the system is coupled to the distal anchor in the left ventricle.

In the embodiment of FIG. 11, the distal anchor 138 is pre-attached to the elongated tether 104 prior to delivery with the delivery catheter 301. Accordingly, once the distal anchor 138 is embedded in the left ventricle LV and the distal anchor 138 is released from the distal anchor shaft 307, the distal end 122 of the elongated tether 104 is attached to the distal anchor 138, as shown in FIG. 12. The distal end 122 is attached to the distal anchor 138 to effectively secure or anchor the distal end 122 of the elongated tether 104 to the left ventricle LV.

Although the elongated tether 104 has been described as coupled to the distal anchors 138 prior to delivery by the delivery catheter 301, this is by way of example and not limitation. It will be understood that the elongated tether 104 may alternatively be delivered separately and coupled to the distal anchor 138 after the distal anchor 138 has been embedded in the left ventricle LV. For example, and not by way of limitation, the elongated tether 104 can include an eyelet at the distal end 122 with the distal anchor shaft 307 disposed through the eyelet of the elongated tether 104. The elongated tether 104 can be deployed from the delivery catheter 301 by a push shaft or other device, and the eyelet and the elongated tether 104 slid distally along the distal anchor shaft 307 to couple to the eyelet of the elongated tether 104 to the distal anchor 138. Once the elongated tether 104 is coupled to the distal anchor 138, the distal anchor 138 is released by the distal anchor shaft 307.

Figure 13:
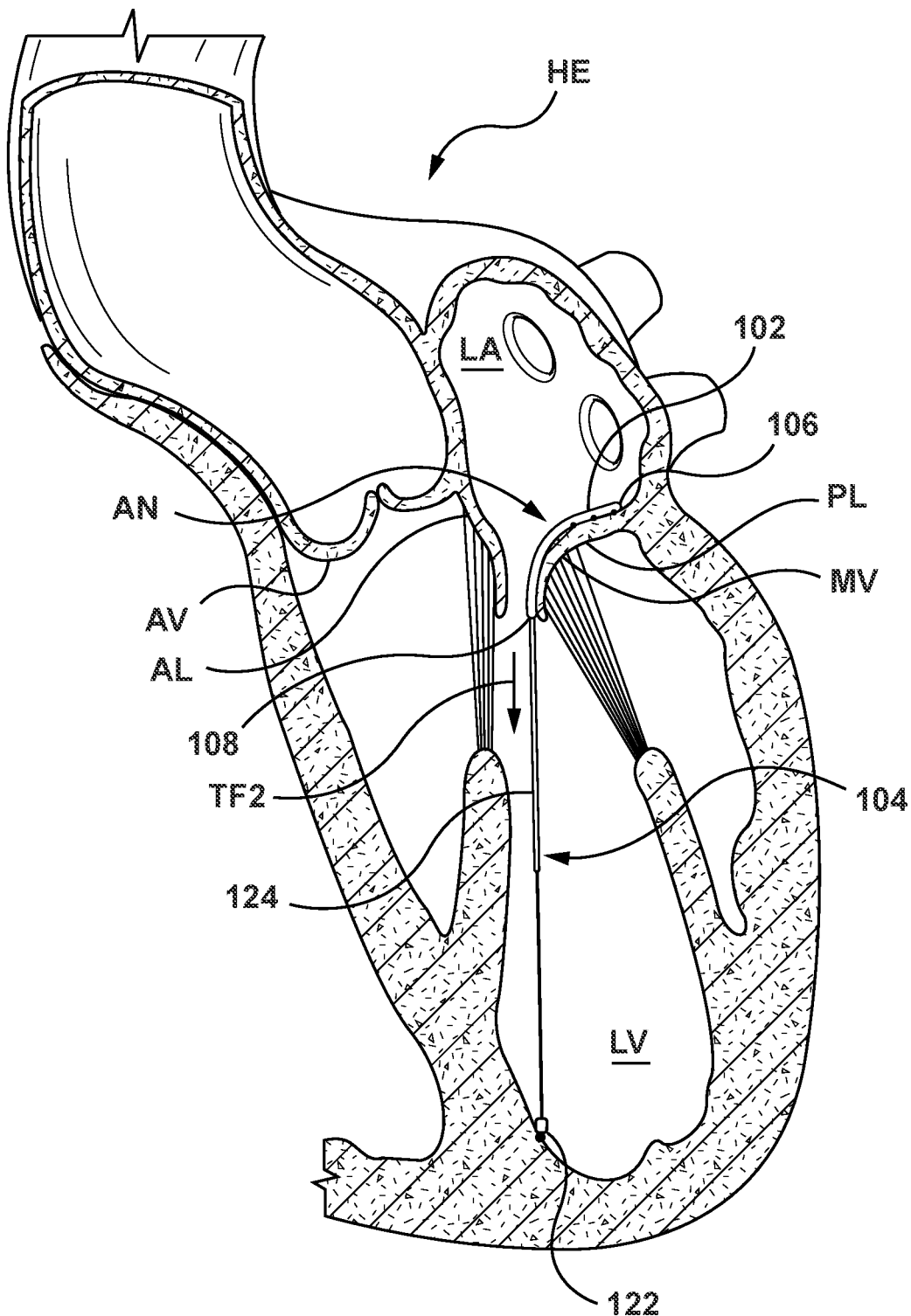
FIG. 13 is a sectional cut-away illustration of the heart illustrating a method step of using the system of FIG. 3A to repair the prolapsed posterior leaflet of the native mitral valve, wherein a tension of the elongated member is applied such that the flexible canopy overlays the posterior leaflet of the native mitral valve.

When the proximal end 106 of the flexible canopy 102 is coupled to the annulus AN and the distal end 122 of the elongated tether 104 is coupled to the left ventricle LV, with the flexible canopy 102 overlaying the posterior leaflet PL, tension is applied and/or adjusted as described above with respect to FIGS. 4 and 5 to apply a tension force on the flexible canopy 102. More precisely, as described above in more detail, the elastic portion 124 of the elongated tether 104 is placed under spring tension and the spring tension on the elastic portion 124 is transferred to the distal end 108 of the flexible canopy 102 as a second tension force TF2 as indicated by the arrow TF2. The second tension force TF2 on the flexible canopy 102 prevents the posterior leaflet PL from prolapsing and insures coaptation of the flexible canopy 102 with the anterior leaflet AL, as shown in FIG. 13.

Figure 14:
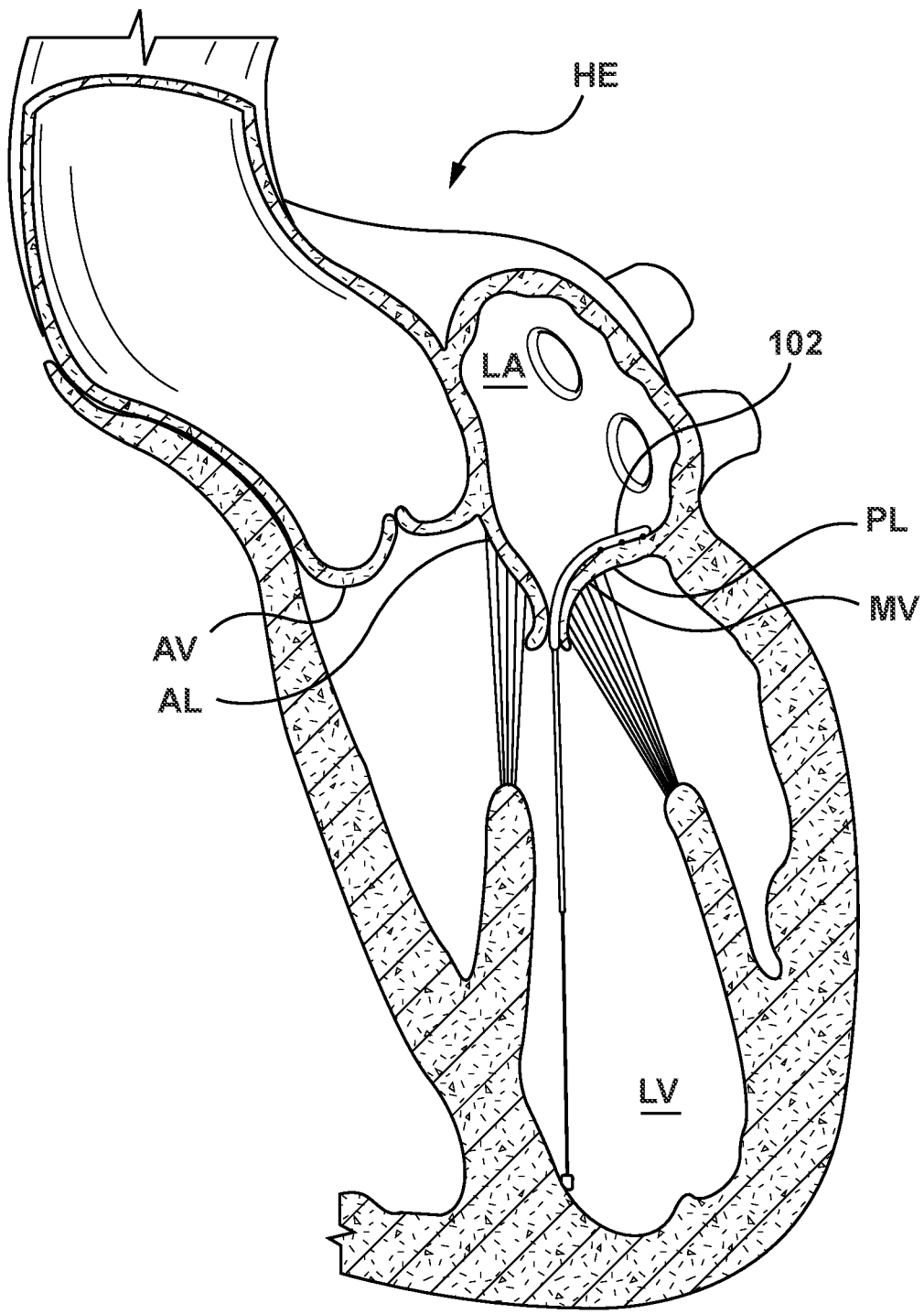
FIG. 14 is a sectional cut-away illustration of the heart illustrating a method step of using the system of FIG. 3A to repair the prolapsed posterior leaflet of the mitral valve, wherein the tension of the elongated tether is adjusted to minimize regurgitation at the mitral valve.

In a next step, the mitral valve MV is checked for valvular regurgitation. Checking for regurgitation of the mitral valve MV may be accomplished by various methods including, but not limited to echocardiogram, to visualize placement of the flexible canopy 102 and prolapse of the posterior leaflet PL of the mitral valve MV. Accordingly, an echogenic coating may be applied to one or more integral portions of the system 100 to aid in visualization. When the mitral valve MV has been checked for valvular regurgitation, the treating clinician may further adjust the tension force on the flexible canopy 102 to minimize valvular regurgitation and optimize coaptation of the flexible canopy 102 with the anterior leaflet AL, as shown in FIG. 14. The steps of checking for valvular regurgitation and readjusting the tension force on the flexible canopy 102 may be repeated to optimize performance of the repaired mitral valve MV. Following delivery, deployment and adjustment of the system 100 at the mitral valve MV (or other desired valve location), the delivery catheter 301 and remaining guidewire (if any) may be removed from the heart 10 and out of the body of the patient.

Image guidance, enhanced echogenicity, or other methods may be used to aid the clinician's delivery and positioning of the system 100. Image guidance, e.g., intracardiac echocardiography (ICE), fluoroscopy, computed tomography (CT), intravascular ultrasound (IVUS), optical coherence tomography (OCT), or another suitable guidance modality, or combination thereof, may be used to aid the clinician's positioning and manipulation of the system 100 at the target native valve region. For example, such image guidance technologies can be used to aid in determining the positioning of the flexible canopy 102 with relation to the underlying, prolapsing native leaflet. In some embodiments, image guidance components (e.g., IVUS, OCT) can be coupled to the distal portion of the delivery catheter 301, a guide catheter, or both to provide three-dimensional images of the area proximate to the target heart valve region to facilitate positioning, orienting and/or deployment of the system 100 within the heart valve region. Accordingly, an echogenic coating may be applied to components of the system to aid in visualization.

Various method steps described above for delivery and deployment of embodiments of the system within a native heart valve of a patient may also be interchanged to form additional embodiments of the present technology. For example, while the method steps described above are presented in a given order, alternative embodiments may perform steps in a different order. The various embodiments described herein may also be combined to provide further embodiments.

Furthermore, while the delivery catheter described above is discussed as being suitable for delivering embodiments of the system to the native mitral valve using a transseptal approach, it will be understood that the delivery catheter may also be suitable for delivering systems for repair of other heart valves (e.g., pulmonary valve, tricuspid valve, etc.) and utilizing other approaches (e.g. retrograde, antegrade). Various arrangements of the delivery catheters suitable for use with embodiments of systems and methods described herein may also be used to deliver other therapeutic or medical tools within body lumens.

While various embodiments have been described above, it should be understood that they have been presented only as illustrations and examples of the present technology, and not by way of limitation. It will be apparent to persons skilled in the relevant art that various changes in form and detail may be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, may be used in combination with the features of any other embodiment. All patents and publications discussed herein are incorporated by reference herein in their entirety.

What is claimed is:

1. A system for treating a native heart valve, the system including a delivery configuration and a deployed configuration, the system comprising:
   a flexible canopy;
   an elongated tether configured to be placed under tension in situ, the elongated tether including an elastic portion and an inelastic portion coupled to the elastic portion, wherein the elastic portion is at least as long as the inelastic portion with a ratio of the elastic portion to the inelastic portion being between 50/50 and 70/30 and a proximal end of the elongated tether is attached to a distal end of the flexible canopy; and a distal anchor configured to be embedded into tissue of a ventricle, wherein a distal end of the elongated tether is coupled to the distal anchor, wherein when the system is in the deployed configuration, a proximal end of the flexible canopy is anchored to an annulus of the heart valve and the distal end of the elongated tether is anchored to tissue of a ventricle via the distal anchor such that the elongated tether is placed under tension.

2. The system of claim 1, wherein the flexible canopy includes a first surface and a second surface opposite the first surface, wherein when the system is in the deployed configuration, the first surface of the flexible canopy overlays to an underlying first surface of a first leaflet of the heart valve, and the system is configured to prevent the first leaflet of the heart valve from prolapsing, and to permit a portion of the second surface of the flexible canopy to coapt with at least an opposing mating portion of a second leaflet of the heart valve.

3. The system of claim 2, further comprising: a frame coupled to a portion of the flexible canopy.

4. The system of claim 2, wherein the flexible canopy is unsupported and does not include a frame coupled thereto.

5. The system of claim 2, wherein the first surface of the flexible canopy includes at least one micro-barb and the at least one micro-barb is configured to couple the first surface of the flexible canopy to the underlying first surface of the first leaflet of the heart valve.

6. The system of claim 1, wherein the inelastic portion of the elongated tether is positioned distal of the elastic portion of the elongated tether.

7. The system of claim 1, wherein the elastic portion of the elongated tether is positioned distal of the inelastic portion of the elongated tether.

8. The system of claim 1, wherein the elastic portion of the elongated tether is longer than the inelastic portion of the elongated tether.

9. The system of claim 1, wherein the elastic portion of the elongated tether is a spring.

10. The system of claim 1, wherein the distal anchor is helical.

11. A system for treating a native heart valve, the system including a delivery configuration and a deployed configuration, the system comprising:

a flexible canopy and a frame attached to the flexible canopy to provide structural support thereto;

an elongated tether configured to be placed under tension in situ, the elongated tether including an elastic portion and an inelastic portion coupled to the elastic portion, wherein the elastic portion is at least as long as the inelastic portion with a ratio of the elastic portion to the inelastic portion being between 50/50 and 70/30 and a proximal end of the elongated tether is attached to a distal end of the flexible canopy; and a distal anchor configured to be embedded into tissue of a ventricle, wherein a distal end of the elongated tether is coupled to the distal anchor, wherein when the system is in the deployed configuration, a proximal end of the flexible canopy is anchored to an annulus of the heart valve and the distal end of the elongated tether is anchored to tissue of a ventricle via the distal anchor such that the elongated tether is placed under tension.

12. The system of claim 11, wherein the flexible canopy has a first surface and a second surface opposite the first surface, wherein when the system is in the deployed configuration, the first surface of the flexible canopy overlays an underlying first surface of a first leaflet of the heart valve, and the system is configured to prevent the first leaflet of the heart valve from prolapsing, and to permit a portion of the second surface of the flexible canopy to coapt with at least an opposing mating portion of a second leaflet of the heart valve.

13. The system of claim 12, wherein the first surface of the flexible canopy includes at least one micro-barb and the at least one micro-barb is configured to couple the first surface of the flexible canopy to the underlying first surface of the first leaflet of the heart valve.

14. The system of claim 11, wherein the inelastic portion of the elongated tether is positioned distal of the elastic portion of the elongated tether.

15. The system of claim 11, wherein the elastic portion of the elongated tether is positioned distal of the inelastic portion of the elongated tether.

16. The system of claim 11, wherein the elastic portion of the elongated tether is longer than the inelastic portion of the elongated tether.

17. The system of claim 11, wherein the elastic portion of the elongated tether is a spring.

18. The system of claim 11, wherein the distal anchor is helical.

19. The system of claim 11, wherein the frame has a shape that follows a perimeter of the flexible canopy.

20. The system of claim 11, wherein the frame is formed from a nickel titanium alloy.

* * * * *